United States Patent
Lin et al.

(10) Patent No.: US 9,956,408 B2
(45) Date of Patent: *May 1, 2018

(54) METHOD FOR REDUCING SPASTICITY AND NON-TRANSITORY COMPUTER-READABLE MEDIUM THEREOF

(71) Applicant: GiMer Medical Co., Ltd., New Taipei (TW)

(72) Inventors: Wei-Tso Lin, New Taipei (TW); Kuo-Hsiang Lu, New Taipei (TW)

(73) Assignee: Gimer Medical Co. Ltd., New Taipei (TW)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/334,932

(22) Filed: Oct. 26, 2016

(65) Prior Publication Data

US 2017/0043163 A1    Feb. 16, 2017

Related U.S. Application Data

(63) Continuation-in-part of application No. 14/049,235, filed on Oct. 9, 2013, now Pat. No. 9,526,889, and a (Continued)

(30) Foreign Application Priority Data

Oct. 1, 2014    (TW) .............. 103217434 U

(51) Int. Cl.
*A61N 1/36*    (2006.01)
*A61N 1/05*    (2006.01)
*A61N 1/06*    (2006.01)

(52) U.S. Cl.
CPC ....... *A61N 1/36067* (2013.01); *A61N 1/0551* (2013.01); *A61N 1/06* (2013.01); *A61N 1/36071* (2013.01); *A61N 1/36171* (2013.01)

(58) Field of Classification Search
CPC .............. A61N 1/36117; A61N 1/0551; A61N 1/0556; A61N 1/06; A61N 1/36071
See application file for complete search history.

(56) References Cited

U.S. PATENT DOCUMENTS 4,398,537 A    8/1983    Holmbo
5,776,170 A    7/1998    MacDonald
(Continued)

FOREIGN PATENT DOCUMENTS

CN    1138829 A    12/1996
CN    101610810 A    12/2009
(Continued)

OTHER PUBLICATIONS

Yeh et al., "A novel continuous visual analog scale model derived from pain-relief demand index via Hilbert Huang transform for postoperative pain," Journal of Medical and Biological Engineering, 31(3), Jan. 2011, pp. 169-176.

(Continued)

*Primary Examiner* — Christopher D Koharski
*Assistant Examiner* — Natasha Patel
(74) *Attorney, Agent, or Firm* — Muncy, Geissler, Olds & Lowe, P.C.

(57) ABSTRACT

A method for reducing spasticity applied with an electrical stimulation device to electrically stimulate a target zone of an organism suffering from spasticity. The electrical stimulation device comprises at least one electrical stimulation unit. The electrical stimulation unit includes at least one first electrode and at least one second electrode. The method includes the following steps. The electrical stimulation unit is placed near the target zone. The electrical stimulation unit generates an electrical stimulation signal and the electrical stimulation signal is introduced to the target zone so as to stimulate the target zone. An electric field is generated (Continued)

between the first electrode and the second electrode and covers the target zone. The strength of the electric field ranges from 100 V/m to 1000 V/m.

18 Claims, 35 Drawing Sheets

Related U.S. Application Data continuation-in-part of application No. 14/872,806, filed on Oct. 1, 2015, now Pat. No. 9,770,592, and a continuation-in-part of application No. 14/925,379, filed on Oct. 28, 2015, which is a continuation-in-part of application No. 14/049,235, filed on Oct. 9, 2013, now Pat. No. 9,526,889.

(56) References Cited

U.S. PATENT DOCUMENTS

| | | |
|---|---|---|
| 6,246,912 B1 | 6/2001 | Sluijter |
| 7,330,762 B2 | 2/2008 | Boveja et al. |
| 7,337,006 B2 | 2/2008 | Kim et al. |
| 7,447,546 B2 | 11/2008 | Kim et al. |
| 7,450,993 B2 | 11/2008 | Kim et al. |
| 7,502,651 B2 | 3/2009 | Kim et al. |
| 7,580,753 B2 | 8/2009 | Kim et al. |
| 8,082,039 B2 | 12/2011 | Kim et al. |
| 8,170,675 B2 | 5/2012 | Alataris et al. |
| 8,209,021 B2 | 6/2012 | Alataris et al. |
| 8,229,565 B2 | 7/2012 | Kim et al. |
| 8,249,701 B2 | 8/2012 | Imran et al. |
| 8,255,057 B2 | 8/2012 | Fang et al. |
| 8,311,639 B2 | 11/2012 | Parker et al. |
| 8,355,792 B2 | 1/2013 | Alataris et al. |
| 8,355,797 B2 | 1/2013 | Caparso et al. |
| 8,359,102 B2 | 1/2013 | Alataris et al. |
| 8,359,103 B2 | 1/2013 | Alataris et al. |
| 8,380,318 B2 | 2/2013 | Kishawi et al. |
| 8,396,559 B2 | 3/2013 | Alataris et al. |
| 8,423,147 B2 | 4/2013 | Alataris et al. |
| 8,428,748 B2 | 4/2013 | Alataris et al. |
| 8,457,759 B2 | 6/2013 | Parker et al. |
| 8,498,710 B2 | 7/2013 | Walker et al. |
| 8,509,905 B2 | 8/2013 | Alataris et al. |
| 8,509,906 B2 | 8/2013 | Walker et al. |
| 8,768,472 B2 | 7/2014 | Fang et al. |
| 2004/0162590 A1* | 8/2004 | Whitehurst ........ A61N 1/36071 607/17 |
| 2005/0154425 A1 | 7/2005 | Boveja |
| 2006/0116721 A1* | 6/2006 | Yun ................ A61N 1/3605 607/2 |
| 2006/0149337 A1* | 7/2006 | John ................ A61N 1/36082 607/45 |
| 2007/0021803 A1 | 1/2007 | Deem et al. |
| 2007/0129760 A1* | 6/2007 | Demarais ........... A61B 18/1492 607/2 |
| 2009/0062886 A1 | 3/2009 | O'Handley et al. |
| 2009/0270943 A1 | 10/2009 | Maschino |
| 2010/0010567 A1* | 1/2010 | Deem ................ A61N 1/0412 607/46 |
| 2010/0152811 A1 | 6/2010 | Flaherty |
| 2010/0298905 A1* | 11/2010 | Simon ............... A61N 1/3601 607/40 |
| 2011/0130804 A1 | 6/2011 | Lin et al. |
| 2012/0029591 A1* | 2/2012 | Simon .................... A61N 1/40 607/42 |
| 2012/0035687 A1 | 2/2012 | Lu |
| 2012/0296389 A1 | 11/2012 | Fang et al. |
| 2013/0079862 A1 | 3/2013 | Ellrich |
| 2013/0096643 A1 | 4/2013 | Fang |
| 2013/0116752 A1 | 5/2013 | Parker et al. |
| 2013/0138178 A1 | 5/2013 | Lin et al. |
| 2013/0144359 A1 | 6/2013 | Kishawi et al. |
| 2013/0317564 A1 | 11/2013 | Lin et al. |
| 2014/0039579 A1 | 2/2014 | Mashiach et al. |
| 2014/0257437 A1 | 9/2014 | Simon |
| 2015/0100112 A1 | 4/2015 | Chang et al. |
| 2015/0174397 A1* | 6/2015 | Bhadra .............. A61N 1/0556 607/117 |

FOREIGN PATENT DOCUMENTS

| | | |
|---|---|---|
| CN | 102120060 A | 7/2011 |
| CN | 102939066 A | 2/2013 |
| WO | WO 95/19804 | 7/1995 |
| WO | 2008/094345 A1 | 8/2008 |

OTHER PUBLICATIONS

Chi-Heng Chang, "Feasibility study of implantable pulsed-radiofrequency stimulator with verification on sciatica rat model", Institute of Biomedical Engineering National Taiwan University, 2009, 2 pgs.

Lin et al., "The effect of high and low frequency electroacupuncture in pain after lower abdominal surgery," Pain, 99 (2002), pp. 509-514.

Wen et al., "A minimal stress model for the assessment of electroacupuncture analgesia in rats under halothane," European Journal of Pain, 11 (2007), pp. 733-742.

Zhuang et al., "Role of the CX3CR1/p38 MAPK pathway in spinal microglia for the development of neuropathic pain following nerve injury-induced cleavage of fractalkine," Brain Behav Immun., 21(5), Jul. 2007, pp. 642-651.

Wen et al., "Nerve conduction blockade in the sciatic nerve prevents but does not reverse the activation of p38 mitogen-activated protein kinase in spinal microglia in the rat spared nerve injury model," Anesthesiology, 107 (2007), pp. 312-321.

Shieh et al., "A novel fuzzy pain demand index derived from patient-controlled analgesia for postoperative pain," IEEE Transactions on Biomedical Engineering, vol. 54, No. 12, Dec. 2007, pp. 2123-2132.

Shieh et al., Fuzzy Logic: Theory, Programming and Applications, 1$^{st}$ edition, Chapter 7, "Fuzzy logic applied in multidimensional model of postoperative pain derived from patient-controlled analgesia," published by Nova Science Publishers, Jun. 2009, pp. 247-267.

Chiu et al., "Pain control on demand based on pulsed radio-frequency stimulation of the dorsal root ganglion using a batteryless implantable CMOS SoC," IEEE Transactions on Biomedical Circuits and Systems, vol. 4, No. 6, Dec. 2010, pp. 350-359.

Lin et al., IEEE International Solid State Circuits Conference, "ISSCC 2010/Session 12/Emerging Medical Applications/12.1," Feb. 7-11, 2010, pp. 234-236.

Wen et al., "DNIC-mediated analgesia produced by a supramaximal electrical or a high-dose formalin conditioning stimulus: roles of opioid and α2-adrenergic receptors," Journal of Biomedical Science, 17:19, 2010, pp. 1-13.

* cited by examiner delivering first electrical stimulation signal by the electrical stimulation unit to electrically stimulate the target zone, wherein an electric field covering the target zone is generated between the first electrode and the second electrode according to the first electrical stimulation signal, and a strength of the electric field ranges from 100 V/m to 1000 V/m ~ S11

FIG.17B

METHOD FOR REDUCING SPASTICITY AND NON-TRANSITORY COMPUTER-READABLE MEDIUM THEREOF

CROSS REFERENCE TO RELATED APPLICATIONS

This application is a Continuation-in-Part of co-pending application Ser. No. 14/925,379, filed on Oct. 28, 2015, which is a Continuation-in-Part of co-pending application Ser. No. 14/049,235, filed on Oct. 9, 2013, and this application is a Continuation-in-Part of co-pending application Ser. No. 14/872,806, filed on Oct. 1, 2015, for which priority is claimed under 35 U.S.C. § 120; and this application claims priority of Application No. 103217434 filed in Taiwan, R.O.C. on Oct. 1, 2014 under 35 U.S.C. § 119; the entire contents of all of which are hereby incorporated by reference.

BACKGROUND

Technical Field

The invention relates to a method for reducing spasticity and a computer-readable medium utilizing such method.

Related Art

Spasticity is a condition in which there is abnormally high muscle tone (hypertonus) resulted from hyperactive reflex of muscle and in turn means violent and involuntary muscular contraction, accompanied by increased tendon reflex activity and hypertonia. In America, there are about 450 thousand persons suffering from spasticity, and the population is increased in an incremental rate of 10 thousand persons per year. Spasticity is usually caused by the injury of the area of the brain or spinal cord which controls the voluntary movement, such as cerebral trauma and serious brain damage due to car accident, battery, or fall from heights, or cerebrovascular disease (e.g., ischemic brain damage or brain palsy), or may occur secondary to multiple sclerosis (MS), a spinal cord injury, or certain metabolic disorders.

The conventional treatments of spasticity can be classified into three categories. The first category of the treatment of spasticity is to treat with medicine, such as baclofen, diazepam, tizanidine hydrochloride tablets, or injection of phenol drugs (i.e., phenol nerve block). Recently, injecting botulinum toxin to the affected region is also found to be effective in treating spasticity. The second category is surgery, such as selective dorsal rhizotomy (SDR), tendon lengthening (i.e., partial tenotomy, marginal myotomy) or implantation of a drug pump. For example, people who suffer from severe spasticity can receive intrathecal baclofen therapy (ITB therapy) to implant a baclofen pump under the skin to deliver liquid form of baclofen directly to the disordered region of the spinal cord so as to keep a high concentration of baclofen at the targeted region and also avoid side effects resulted from high-dose oral baclofen therapy. The third category is to ameliorate spastic symptoms through physical therapies, such as stretch exercise, strength training, endurance training, range of motion exercise, joint passive motion, or reflex inhibition posture.

However, there is some deficiency in each of those abovementioned treatments of spasticity. For drug treatment, it usually accompanied with side effects and increases the burden of some organs of patients, such as liver, stomach, or gastrointestinal tract. Long-term treatment of drugs also increases the tendency for patient to over rely on the drugs. For surgical treatment, the deficiency includes allergic reactions to anesthesia, postoperative complications, infections, recurrence of symptoms, or damages to other nerves. More importantly, it may cause fear and psychological pressure of patients and also make patients to worry about the recovery situation after surgery and the possibility of recurrence. For the treatment of physical therapies, although it may help to ameliorate spastic symptoms, it still takes a long time to show a perceptible improvement.

As shown in FIG. 22, in the rat model of neuropathic pain provided by Ronen Shechter et al. (Ronen Shechter et al. (2013, August), Conventional and Kilohertz-frequency Spinal Cord Stimulation Produces Intensity- and Frequency-dependent Inhibition of Mechanical Hypersensitivity in a Rat Model of Neuropathic Pain, ANESTHESIOLOGY, 119 (2), 422-32), the rats with spinal cord injuries were received an electrical stimulation with frequency of 50 Hz to 10 kHz for thirty minutes (80% MoT, constant current, current intensity 0.6 mA-0.7 mA). The paw withdraw thresholds started to drop at 30 minutes after end of the electrical stimulation. Also, it is noted that the paw withdraw thresholds returned to pre-stimulation level at 5 days after the last electrical stimulation. In other words, such conventional electrical stimulation did not provide a long term effect. Patients may have to receive such electrical stimulation for every 4-5 days (or even several times for one day) so as to continuously ameliorate the symptoms caused by neural hypersensitivity. However, such treatment will make patients more and more uncomfortable and also increase the inconvenience of the treating course.

Therefore, it is important to provide a method for reducing spasticity which can effectively ameliorate spastic symptoms with long term effects, without the side effects caused by drugs, and also reduce the possibility of infection caused by operation.

SUMMARY

An aspect of the disclosure is to provide a method for reducing spasticity and the computer-readable medium thereof which can effectively ameliorate spastic symptoms with long term effects, without the side effects caused by drugs, and also reduce the possibility of infection caused by operation.

A method for reducing spasticity is provided herein. The method is applied to electrically stimulate a target zone of an organism by an electrical stimulation device. The electrical stimulation device includes at least an electrical stimulation unit and the electrical stimulation unit includes at least a first electrode and a second electrode. The method comprises the following steps: placing the electrical stimulation unit near the target zone; and delivering a first electrical stimulation signal by the electrical stimulation unit to electrically stimulate the target zone. An electric field covering the target zone is generated between the first electrode and the second electrode according to the first electrical stimulation signal, and a strength of the electric field ranges from 100 V/m to 1000 V/m.

In one embodiment, the first electrical stimulation signal is a pulse signal and its pulse repetition frequency ranges from 0 to 1 KHz.

In one embodiment, the frequency of the first electrical stimulation signal ranges from 200 KHz to 1000 KHz.

In one embodiment, the frequency of the first electrical stimulation signal ranges from 200 KHz to 450 KHz or ranges from 550 KHz to 1000 KHz.

In one embodiment, the frequency of the first electrical stimulation signal comprises a plurality of pulse signals, and the plurality of pulse signals have a duration time ranging from 1 to 250 ms.

In one embodiment, the voltage of the first electrical stimulation signal ranges from −10V to −1V or ranges from 1V to 10V.

In one embodiment, the current of the first electrical stimulation signal ranges from 2 mA to 50 mA.

In one embodiment, the first and second electrodes are separated by a first distance which ranges from 3 mm to 7 mm, and the first and second electrodes are at least at a second distance away from the target zone, and the second distance is no more than 10 mm.

In one embodiment, the first electrical stimulation signal is adapted to block the neurotransmission in the target zone.

In one embodiment, the target zone is brain, spinal cord, ventral root nerve, root nerve, dorsal root ganglion and/or spinal dorsal horn.

In one embodiment, the electrical stimulation unit further delivers a low electrical stimulation signal which is not higher than 1 KHz.

In one embodiment, the organism receives the electrical stimulation signal for a second time at at least 24 hours after receiving the electrical signal for a first time.

A non-transitory computer-readable medium is also provided herein. The non-transitory computer-readable medium stores one or more instructions which are configured to be executed by an electrical stimulation device to electrically stimulate a target zone of an organism who suffers from spasticity so as to reduce spasticity of the organism. The electrical stimulation device includes at least an electrical stimulation unit, and the electrical stimulation unit includes at least a first electrode and a second electrode. When the instructions are executed by the electrical stimulation device, the electrical stimulation device execute the following steps: delivering a first electrical stimulation signal by the electrical stimulation unit to electrically stimulate the target zone. An electric field covering the target zone is generated between the first electrode and the second electrode according to the first electrical stimulation signal, and a strength of the electric field ranges from 100 V/m to 1000 V/m.

In one embodiment, the first electrical stimulation signal is a pulse signal and its pulse repetition frequency ranges from 0 to 1 KHz.

In one embodiment, the frequency of the electrical stimulation signal ranges from 200 KHz to 1000 KHz.

As mentioned above, in the method for reducing spasticity and the non-transitory computer-readable medium according to the disclosure, a first electrical stimulation signal is delivered by the electrical stimulation unit of the electrical stimulation device so as to generate an electric field between the first electrode and the second electrode. The electric field covers a target zone of an organism who suffers from spasticity. Such method and non-transitory computer-readable medium can effectively ameliorate spastic symptoms with long term effects, without the side effects caused by drugs, and also reduce the possibility of infection caused by operation.

BRIEF DESCRIPTION OF THE DRAWINGS

The embodiments will become more fully understood from the detailed description and accompanying drawings, which are given for illustration only, and thus are not limitative of the present invention, and wherein:

FIG. 17B is a flow chart showing the process executed by the computer-readable medium according to another embodiment;

DETAILED DESCRIPTION OF THE INVENTION

The embodiments of the invention will be apparent from the following detailed description, which proceeds with reference to the accompanying drawings, wherein the same references relate to the same elements.

Figure 1A:
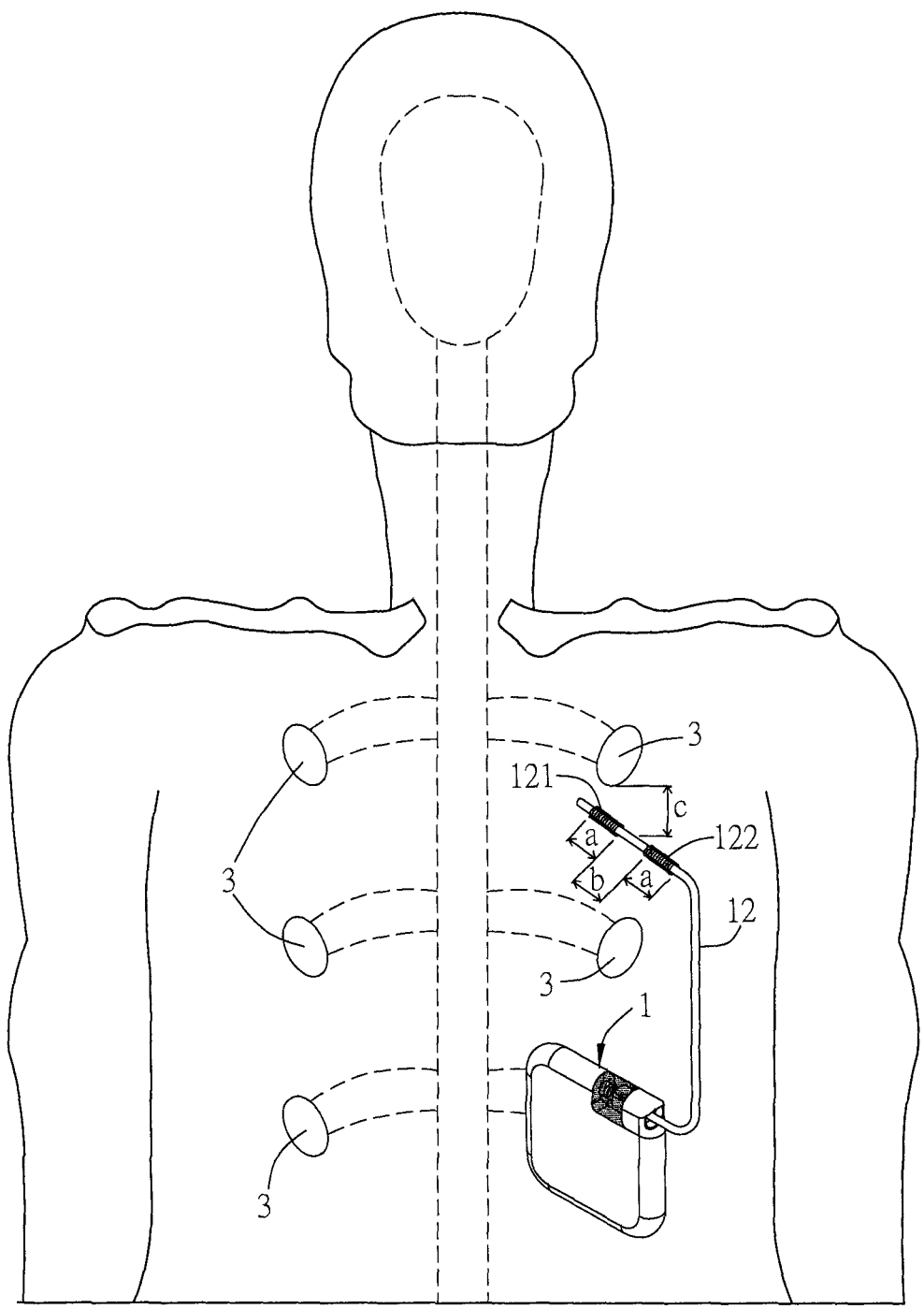
FIG. 1A is a schematic diagram showing the electrical stimulation device applied to the dorsal root ganglion according to the first embodiment.

FIG. 1A is a schematic diagram showing the electrical stimulation device applied to the dorsal root ganglion according to the first embodiment. Referring to FIG. 1A, an electrical stimulation device 1 is applied to electrically stimulate a target zone of an organism. In the embodiment, the target zone is dorsal root ganglion 3 for example. Alternatively, the target zone may be for example but not limited to brain, vertebral column, ventral root nerve, root nerve and/or spinal dorsal horn of an organism. The vertebral column may be cervical vertebrae, thoracic vertebrae, lumbar vertebrae, sacral vertebrae, or caudal vertebrae for example. The following paragraphs will describe the elements and applications of the electrical stimulation device 1.

FIG. 1A is a schematic diagram showing the electrical stimulation device applied to the dorsal root ganglion according to the first embodiment. Referring to FIG. 1A, an electrical stimulation device 1 is applied to electrically stimulate a target zone of an organism. In the embodiment, the target zone is dorsal root ganglion 3 for example. Alternatively, the target zone may be for example but not limited to brain, vertebral column, ventral root nerve, root nerve and/or spinal dorsal horn of an organism. The vertebral column may be cervical vertebrae, thoracic vertebrae, lumbar vertebrae, sacral vertebrae, or caudal vertebrae for example. The following paragraphs will describe the elements and applications of the electrical stimulation device 1.

For the sake of clarity regarding the step details of the method, the circuits and interaction of the electrical stimulation device 1 and the controller 2 are explained first in the following paragraphs. Then, the following paragraphs describe electrically stimulating the target zone of the organism by the electrical stimulation device 1 of the embodiment. However, the descriptions in the following embodiments are exemplary but not intended to limit the scope of the invention.

Figure 1B:
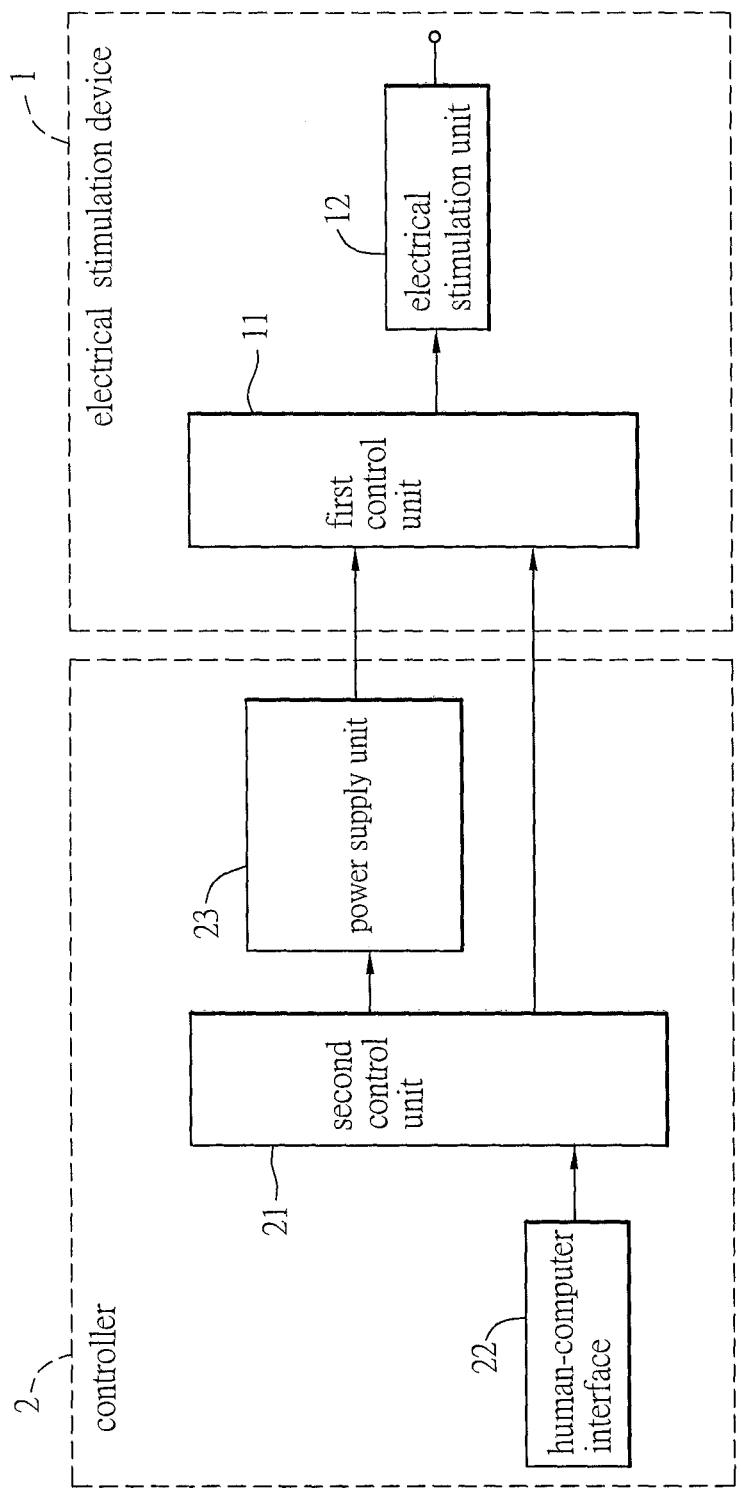
FIG. 1B is a circuit block diagram of the electrical stimulation device and the controller in FIG. 1A.

FIG. 1B is a circuit block diagram of the electrical stimulation device 1 and the controller 2 in FIG. 1A. Referring to FIG. 1B, a controller 2 provides configuration parameters and supplies energy for the electrical stimulation device 1. Because the controller 2 does not need to be implanted in the organism, it may be called the external controller 2. Elements of the electrical stimulation device 1 and the controller 2 and their relationships will be described in the following paragraphs.

In the embodiment, the electrical stimulation device 1 includes a first control unit 11 and an electrical stimulation unit 12. The electrical stimulation unit 12 is coupled to the first control unit 11. The controller 2 includes a second control unit 21, a human-computer interface 22 and a power supply unit 23. The human-computer interface 22 is coupled to the second control unit 21. The power supply unit 23 is also coupled to the second control unit 21 and acts as the power source of the controller 2. The power supply unit 23 may be a battery or a rechargeable battery, or it may be a power adapter connected to mains electricity to supply electrical power.

In the embodiment, the user may use the human-computer interface 22 to operate the controller 2. Before beginning, the system default values of the controller 2 is initialized. Then, the user may also use the human-computer interface 22 to input the required configuration parameters to the second control unit 21. In the embodiment, the human-computer interface 22 may be for example but not limited to touch button, touch panel, physical button or their combination. The second control unit 21 instructs the power supply unit 23 to supply DC power to the elements of the electrical stimulation device 1 (for example the electrical stimulation unit 12) to operate.

The first control unit 11 and the second control unit 21 may be implemented with digital circuit such as IC (integrated circuit) or implemented with analog circuit. For example, IC may be a micro-processor, a MCU (microprocessor control unit), a programmable logic gate array (for example, field-programmable gate array, FPGA, or complex programmable logic devices, CPLD) or ASIC (application-specific integrated circuit). In the embodiment, it is a MCU for example but not limited thereto.

In the embodiment, the electrical stimulation device 1 is an implantable electrical stimulation device for example. The implantable electrical stimulation device means that at least one portion of the element of the electrical stimulation device 1 is implanted in the individual body (e.g., subcutaneous). Moreover, the electrical stimulation device 1 may be changed to a transcutaneous electrical stimulation device depending on the symptom and requirement of the patient. In the embodiment, the electrical stimulation unit 12 is adapted to be implanted in the individual. The first control unit 11 may be implanted within the individual or disposed outside the individual depending on actual or design requirement. If the electrical stimulation unit 12 is prepared to be implanted into one individual, it is better to implant the device in near the dorsal root ganglion of the spinal nerve relevant to the patient's pain. The individual preferably is an organism, and it may include mammals such as mouse, human, rabbit, cattle, sheep, pig, monkey, dog, cat, etc. Preferably, it is human. For example, it is human.

Figure 2A:
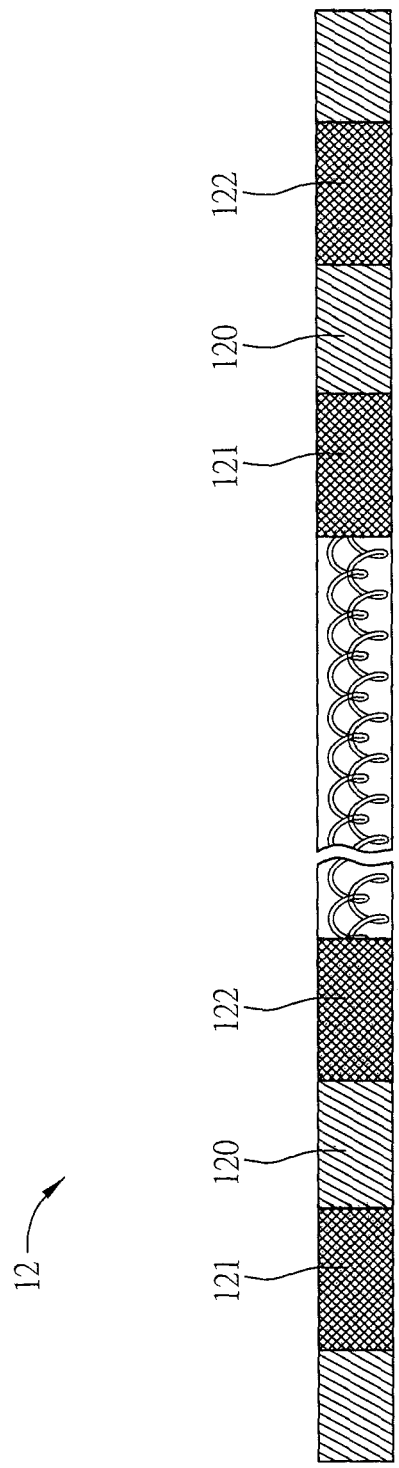
FIGS. 2A and 2B are enlarged diagrams showing a portion of the electrical stimulation unit in FIG. 1A.
Figure 2B:
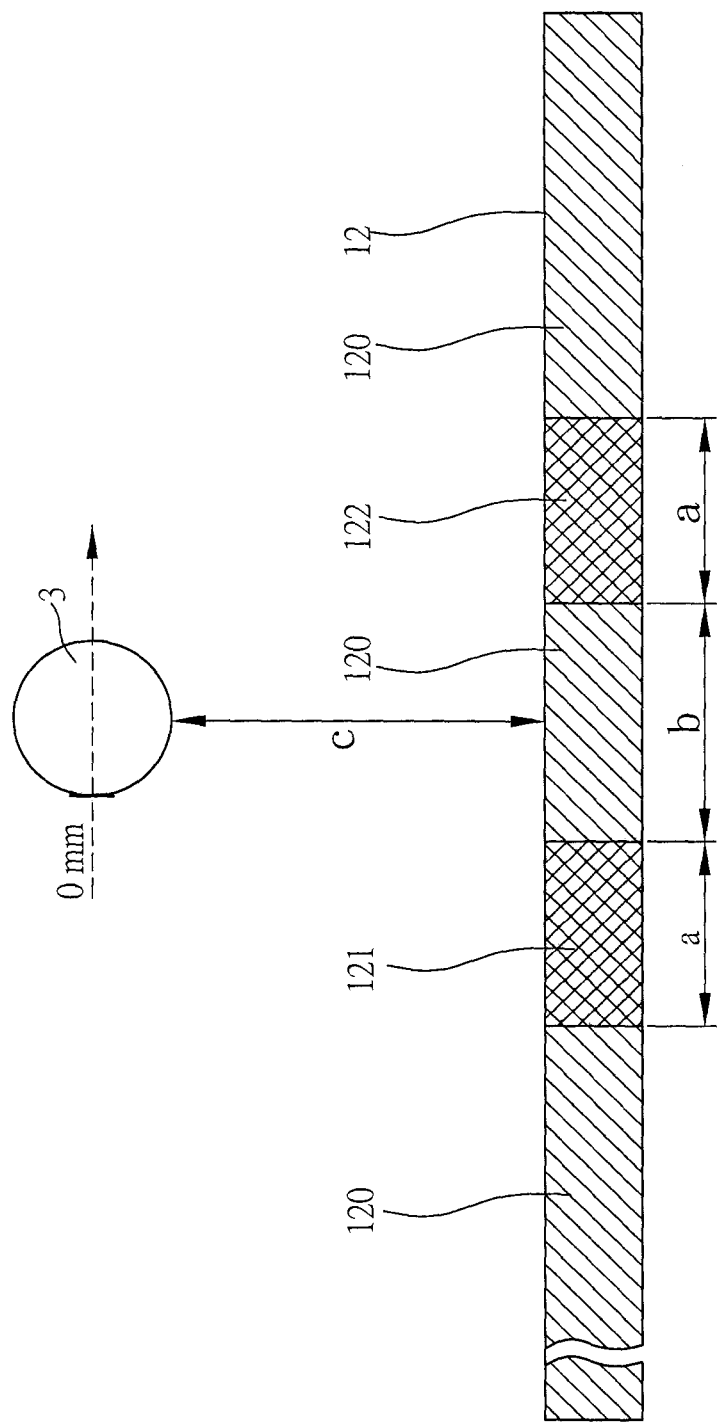

As to the configuration of the electrical stimulation unit 12, referring to FIG. 1A and FIG. 2B, the electrical stimulation unit 12 comprises a flexible transmission lead including at least one first electrode 121 and at least one second electrode 122. In the embodiment, it includes a pair of electrodes, namely a positive electrode 121 and a negative electrode 122 for example. In addition, there are maybe two pairs, three pairs or more than three pairs of electrodes of the electrical stimulation unit 12, and they may be evenly distributed on the transmission lead, namely the electrical stimulation unit 12. The above electrodes operate in bipolar mode to generate an electric field between the first electrode 121 and the second electrode 122. In the embodiment, between the first electrode 121 and the second electrode, there are coils or wires formed from winding coaxial conductor which are electrically connected to the electrodes. For example, the material of the first electrode 121 and the second electrode 122 may be metal for example platinum, silver, gold or other conductive metal. Between the first electrode 121 and the second electrode 122, a zone is defined by the coils or wires which are compactly wound cable electrically connected to the electrodes. The first electrode 121 and the second electrode 122 are disposed at one end of the electrical stimulation unit 12, two contacts 123 acting as the positive and negative electrodes are disposed at the other end of the electrical stimulation unit 12. The two contacts 123 are electrically connected or coupled to the first control unit 11. The first electrode 121 and the second electrode 122 are respectively linked to compactly wound coils, and they are linked to the contacts 123 through the wires. Besides, the wires of the electrical stimulation unit 12 beyond the first electrode 121 and the second electrode 122 is covered by an insulator 120. In FIG. 2A, the insulator 120 is removed to show the coil disposed between the electrodes in the electrical stimulation unit 12.

The range of the individual length a of each electrode depends on actual or design requirement. The electrode length a is between 0.5~6 mm, preferably between 1~4 mm. The individual length a of the first electrode 121 and the second electrode 122 means that the length of the electrode in the direction parallel to the extension direction of the major axis of the cable of the electrical stimulation unit 12 on the condition that it is not implanted and the electrical stimulation unit 12 is horizontally spread. The range of the individual length a of the first electrode 121 and the second electrode 122 depends on actual or design requirement. For example, the length a is between 1~3 mm. The distance b between the first electrode 121 and the second electrode 122 is between 1~7 mm, preferably between 1~4 mm. For example, the distance b of the two adjacent ends of the adjacent first and second electrodes 121, 122 is preferably between 1~4 mm.

A second interval distance c exists between the first electrode 121 and the second electrode 122 of the electrical stimulation unit 1 and the dorsal root ganglion 3. The second interval distance c is defined as the shortest distance from the midpoint of the adjacent first and second electrodes 121, 122 to the dorsal root ganglion 3. In the embodiment, the second interval distance c ranges from 0 to 10 mm, preferably from 0 to 5 mm. If the distance c is 0, the midpoint of the first electrode 121 and the second electrode 122 in the projection direction overlaps the dorsal root ganglion 3.

Figure 1C:
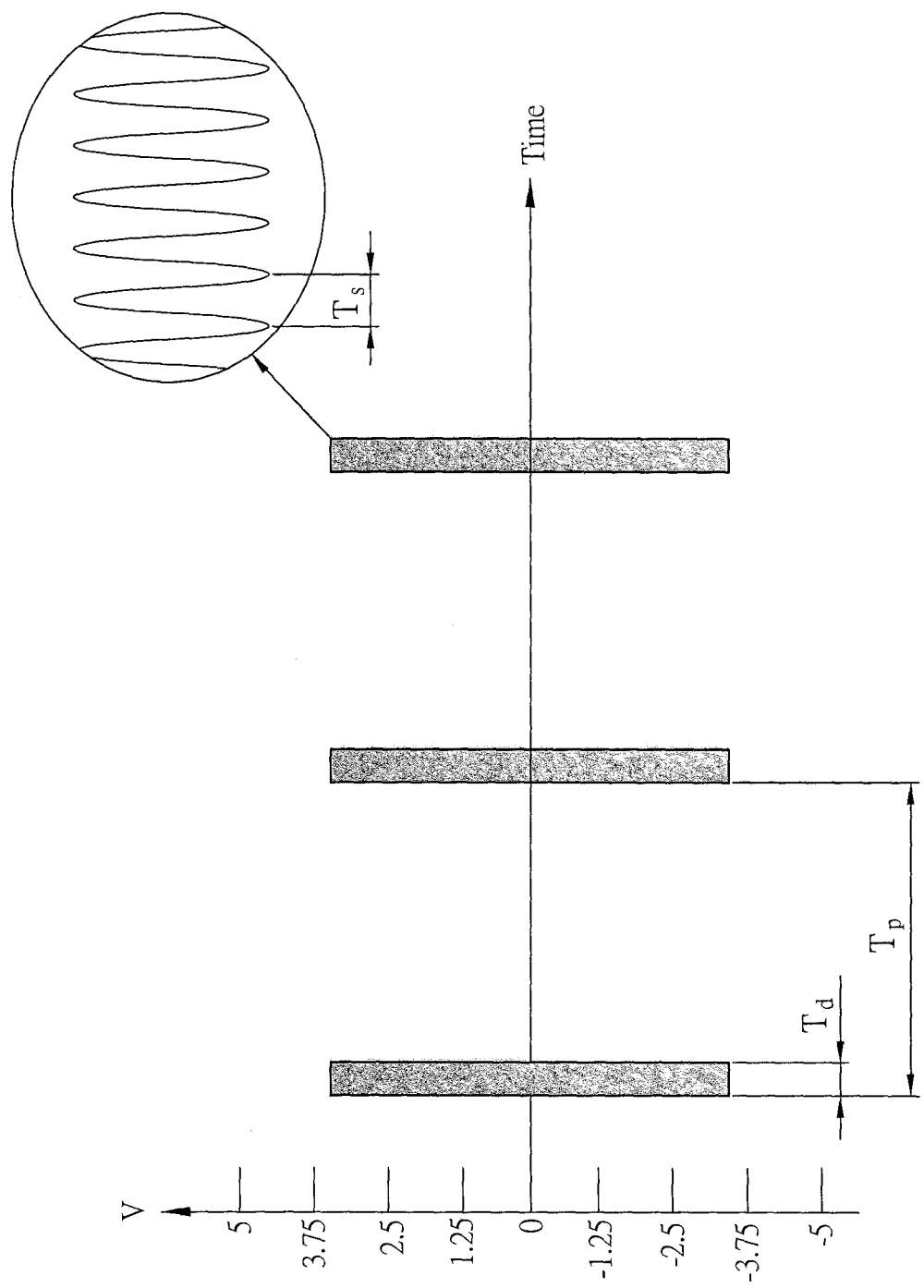
FIG. 1C is a schematic diagram showing the pulse signal of the electrical stimulation signal of the electrical stimulation device in FIG. 1A.

Referring to FIG. 1C, in the embodiment, the electrical stimulation signal outputted from the electrical stimulation device 1 may be a continuous sine wave, a continuous triangle wave or an electrical stimulation signal of high-frequency pulse. If it is an electrical stimulation pulse signal, one pulse cycle time Tp has a plurality of pulse signals and at least one period of rest time. One pulse cycle time is the reciprocal of pulse repetition frequency. The pulse repetition frequency (also called pulse frequency) is between 0~1 KHz, preferably between 1~100 Hz. In the embodiment, the pulse repetition frequency of the electrical stimulation signal is about 2 Hz. Besides, the duration time Td of pulses in one pulse cycle time is between 1~250 ms, preferably between 10~100 ms. In the embodiment it is 25 ms for example.

Referring to FIG. 1C, in the embodiment, the electrical stimulation unit 12 is adapted to transmit a first electrical stimulation signal. For example, the patient (or healthcare workers) uses the controller 2 to set the electrical stimulation frequency, stimulation period, stimulation intensity and/or other parameters of the first electrical stimulation signal. Then, the controller 2 outputs the parameters and energy to the electrical stimulation device 1, and directs the electrical stimulation unit 1 to output signal via the first control unit 11. In the embodiment, the frequency of the first electrical stimulation signal is about 600 KHz. In other words, its stimulation cycle time Ts is about 1.67 μs.

For example, the electrical stimulation device may be chosen to be driven in a constant voltage mode or a constant current mode. The constant voltage mode is safer than the constant current mode, but the intensity in the constant voltage mode is less stable than in the constant current mode. Choosing which mode depends on the target zone to be electrically stimulated. For example, if the target is dorsal column, the constant current mode is chosen. If the target is the dorsal root ganglion, the constant voltage mode is chosen. When the constant voltage mode is chosen for driving, the voltage of the first electrical stimulation signal is constant, and the current of the first electrical stimulation signal varies with the positions and resistances of the first electrode 121 and the second electrode 122. Otherwise, when the constant current mode is chosen for driving, the current of the first electrical stimulation signal is constant, and the voltage of the first electrical stimulation signal varies with the positions and resistances of the first electrode 121 and the second electrode 122. For example, in the constant voltage mode, the voltage of the first electrical stimulation signal ranges from −10V to −1V or from 1V to 10V. Preferably, the voltage of the first electrical stimulation signal ranges from 10V to −3 V or from 3V to 10V. In the constant current mode, the current of the first electrical stimulation signal ranges from 2 mA to 50 mA, preferably from 4 ma to 30 mA.

Besides, the frequency of the first electrical stimulation signal is between 200 KHz~1000 KHz, preferably between 200 KHz~250 KHz, 250 KHz~350 KHz, 350 KHz~450 KHz, 450 KHz~550 KHz, 550 KHz~650 KHz, 650 KHz~750 KHz, 750 KHz~800 KHz, or 800 KHz~1000 KHz. If the selected frequency is between 200 KHz~450 KHz, the device operates in relatively low frequency so it is less risky to produce biological heat for better safety. Otherwise, if the selected frequency is between 550 KHz~1000 KHz, the generated electric field has greater density so its electrical stimulation has better performance. In addition, by adjusting the duration time Td, the amount of the electrical stimulation is adjusted and the time for dissipating the produced biological heat accordingly. For example, if the stimulation intensity is relatively low, the duration time Td may be increased to continuously stimulate. If the stimulation intensity and the frequency are relatively high, the duration time Td may be decreased to raise the time for dissipating heat.

When the electrical stimulation unit 12 receives the first electrical stimulation signal, the first electrode 121 and the second electrode 122 of the electrical stimulation unit 12 accordingly generate an electric field. The distance from the first electrode 121 and the second electrode 122 to the dorsal root ganglion 3 is arranged within the range of the second interval distance c, so the electric field generated by the first electrode 121 and the second electrode 122 covers the dorsal root ganglion 3. In other words, the electric field covers the dorsal root ganglion 3 and its surroundings to electrically stimulate the target dorsal root ganglion 3 with low intensity, low temperature and high frequency. Without destroying the neural cells of the dorsal root ganglion 3, the biomolecule generation by the dorsal root ganglion 3 is suppressed, and the threshold of the target zone of the dorsal root ganglion 3 is also raised. Thus, the neurotransmission capability of the dorsal root ganglion 3 in the target zone is lowered and the neurotransmission is blocked. As a result, the patient feels nerve pain as little as possible.

Furthermore, the patient may feel as little as possible pain on the target zone without generating relative much sensations of paresthesia if applying the electrical stimulation device for electrical stimulation. The patient suffering pains over a long period of time may accept this electrical stimulation treatment which is effective and generates as little as possible sensations of paresthesia. Preferably, the treatment resulting from the electrical stimulation by the electrical stimulation device in the embodiment may keep effective about one week. In other words, the neurotransmission is blocked about one week. Thus, the patient may less frequently receive the electrical stimulation treatment and it is not necessary for him to receive the treatment frequently so he may be more possibly willing to receive the treatment. Because the details can refer to the later experimental examples, they are not repeated here.

Figure 3A:
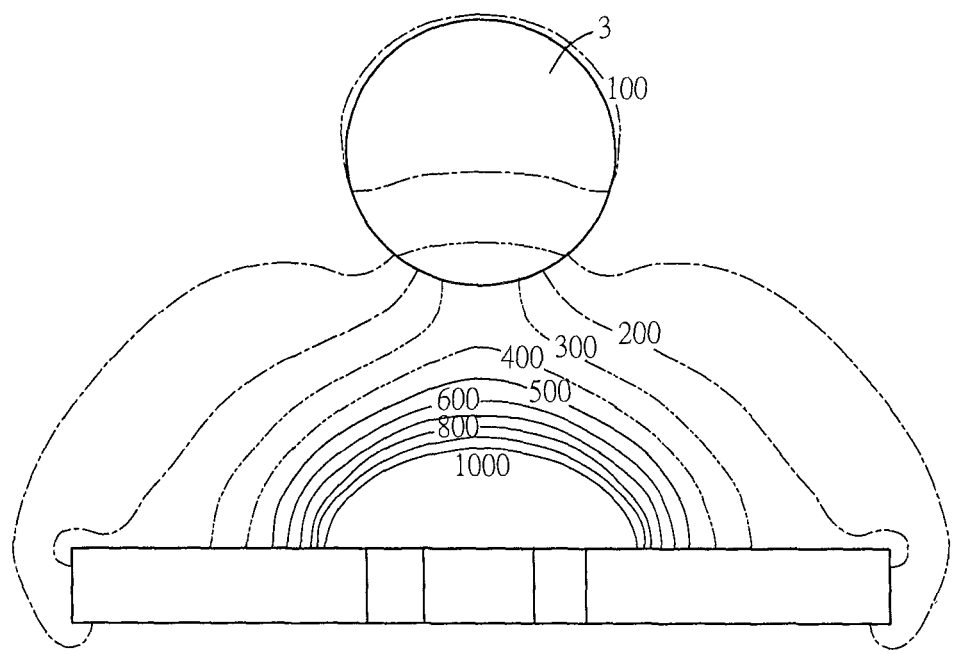
FIGS. 3A to 3E and FIGS. 4A to 4E are schematic diagrams of the electric field simulation of the electrical stimulation device.
Figure 3B:
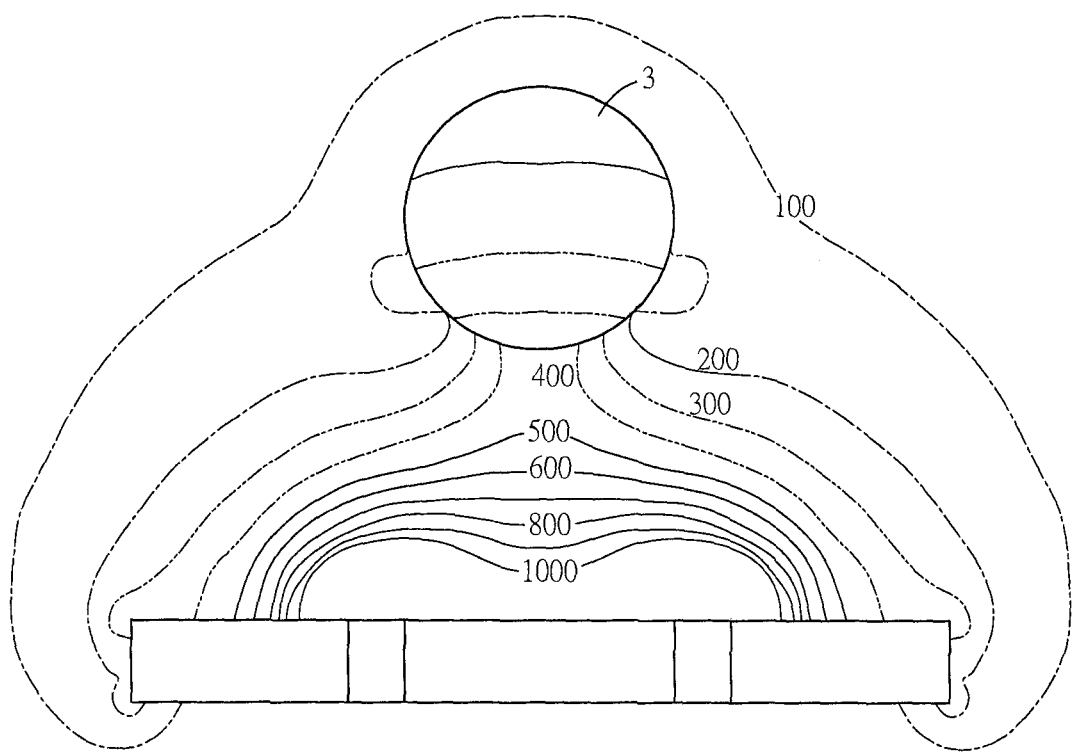
Figure 3C:
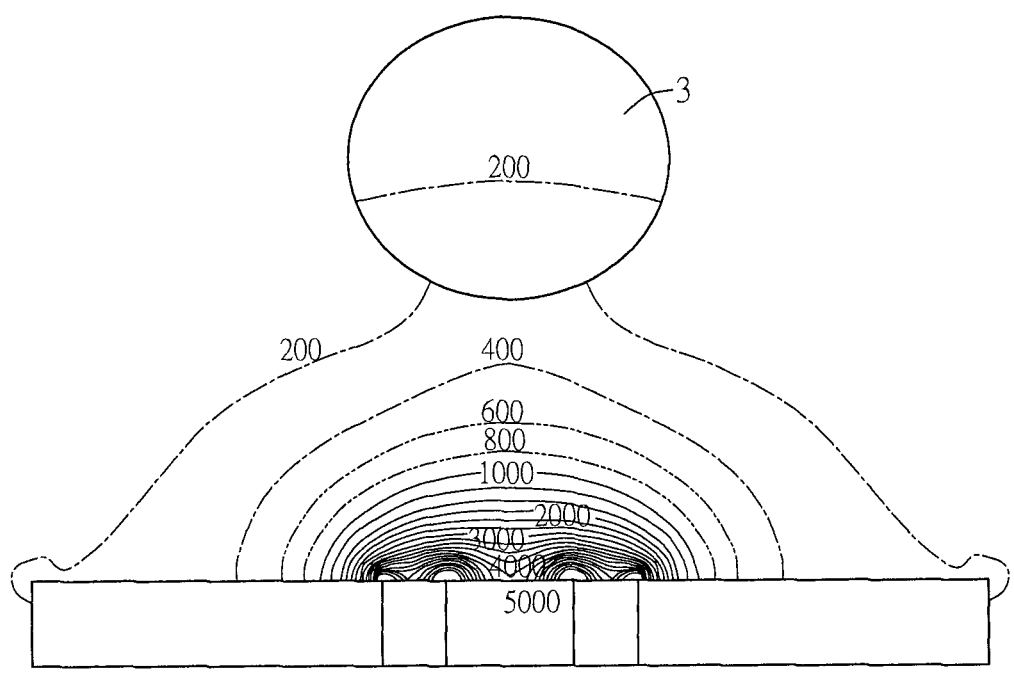
Figure 3D:
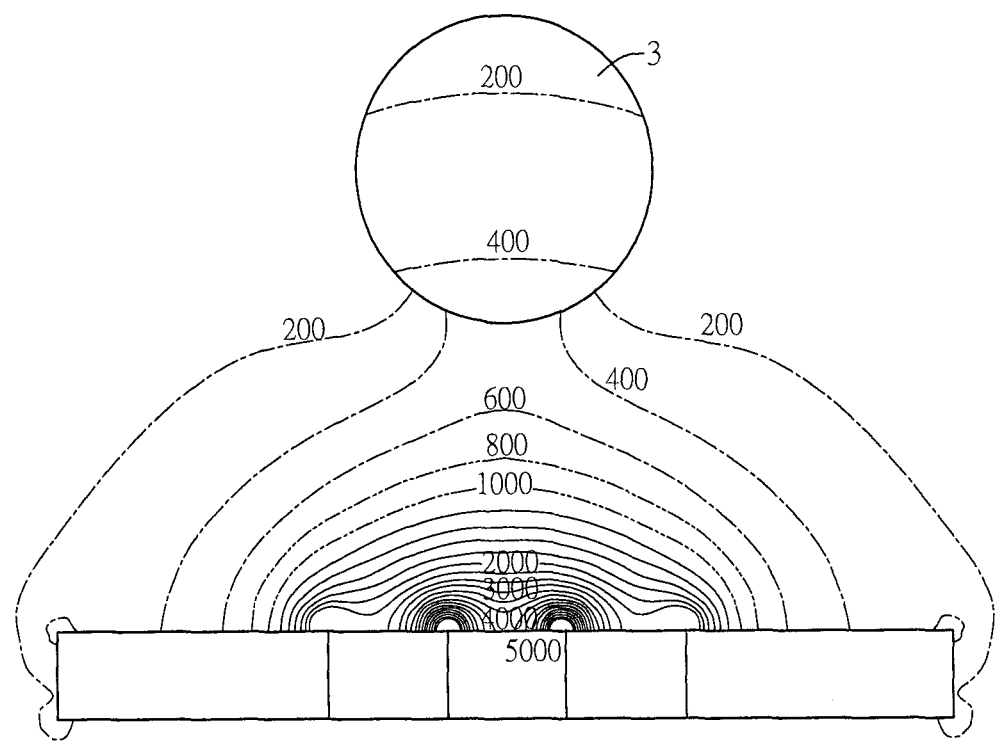
Figure 3E:
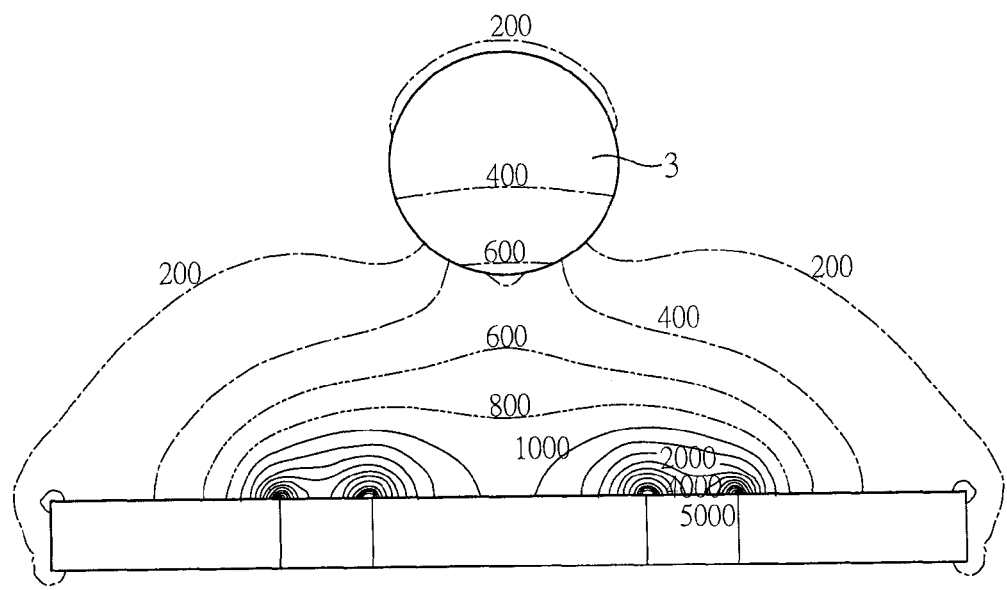

Furthermore, referring to FIG. 3A to FIG. 3D, the field pattern of the electric field is adjusted by adjusting the electrode length a of the first electrode 121 and the second electrode 122, the first interval distance b between the first electrode 121 and the second electrode 122, or the second interval distance c between the first electrode 121, the second electrode 122 and the dorsal root ganglion 3. For example, the voltage of the electrical stimulation signal is 5V, its frequency is 500 KHz, and the distance C is 5 mm. Assuming that the electrode length a and the distance c of the first electrode 121 and the second electrode 122 are constant (a=1 mm, c=5 mm), as smaller the distance b (b=2 mm) between the first electrode 121 and the second electrode 122 as shown in the electric field simulation diagram in FIG. 3, the electric field (the strength of the electric field is 100 V/m~1000 V/m) may only or mainly effectively cover the dorsal root ganglion 3 to be stimulated; as greater the distance b (b=4 mm) between the first electrode 121 and the second electrode 122 as shown in FIG. 3B, the field pattern of the electric field is distributed expandingly and completely cover the dorsal root ganglion 3 to be stimulated (the drawn strength of the electric field is 100 V/m~1000 V/m). Relatively, the electric field strength is more intensive if the position is closer to the electric field of the first electrode 121 and the second electrode 122. As shown in FIG. 3C, it is a distribution diagram of the field pattern that the field pattern of the electric field in FIG. 3A is applied with a more intensive electric field so the strength of the electric field is distributed in the range 100 V/m~5000 V/m. From the figure, as long as the electrode is disposed close enough to the target zone which is to be stimulated (the distance c is between 0~10 mm), the electric field has an effect on it and the electric field with higher intensity is distributed more closer to the surface of the electrode. Then, referring to FIG. 3D and FIG. 3E, the difference between FIG. 3D and FIG. 3C is the electrode length a of the first electrode 121 and the second electrode 122. In FIG. 3D, the electrode length a is changed to 2 mm. From FIG. 3D, it is seen that the electrode becomes longer and the space distribution of the field pattern of the electric field also becomes slightly larger. The difference between FIG. 3E and FIG. 3D is that the distance b between the electrodes is changed to 6 mm on the condition that the electrode length a of the first electrode 121 and the second electrode 122 are both fixed (at 2 mm). As the distance b between the electrodes is increased, the space distribution of the field pattern of the electric field also becomes larger.

Figure 4A:
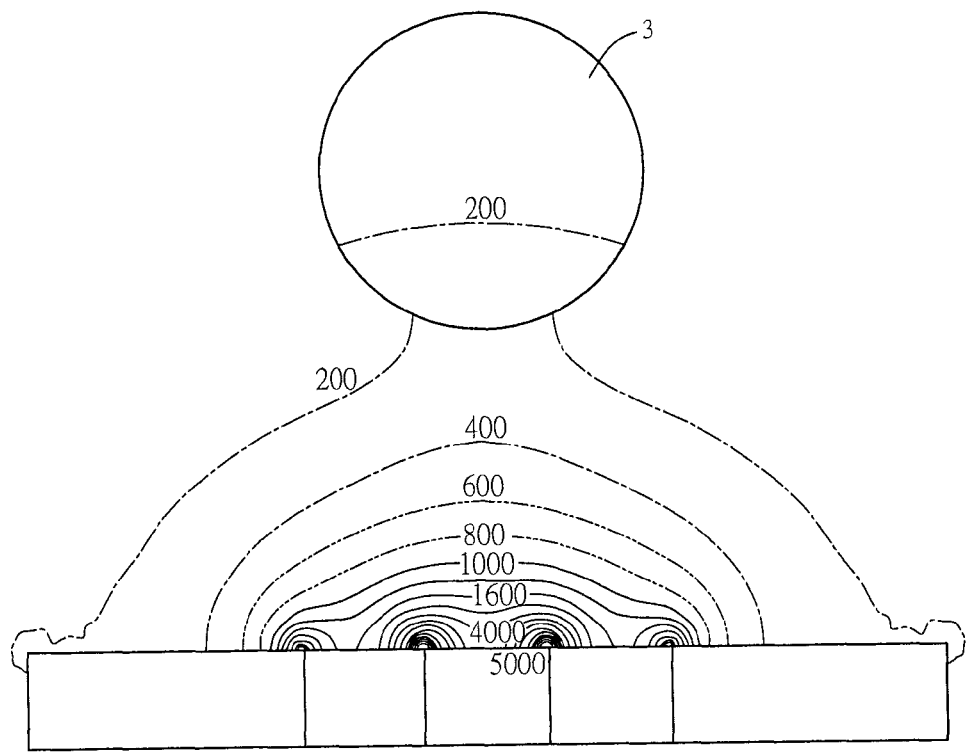
Figure 4B:
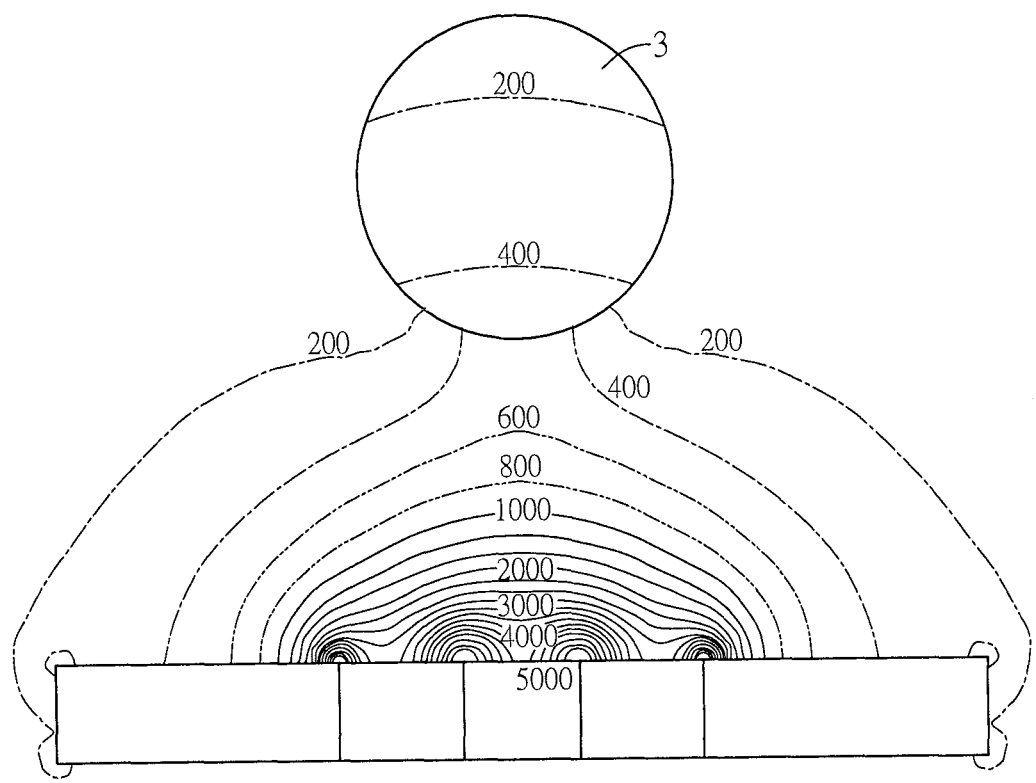
Figure 4C:
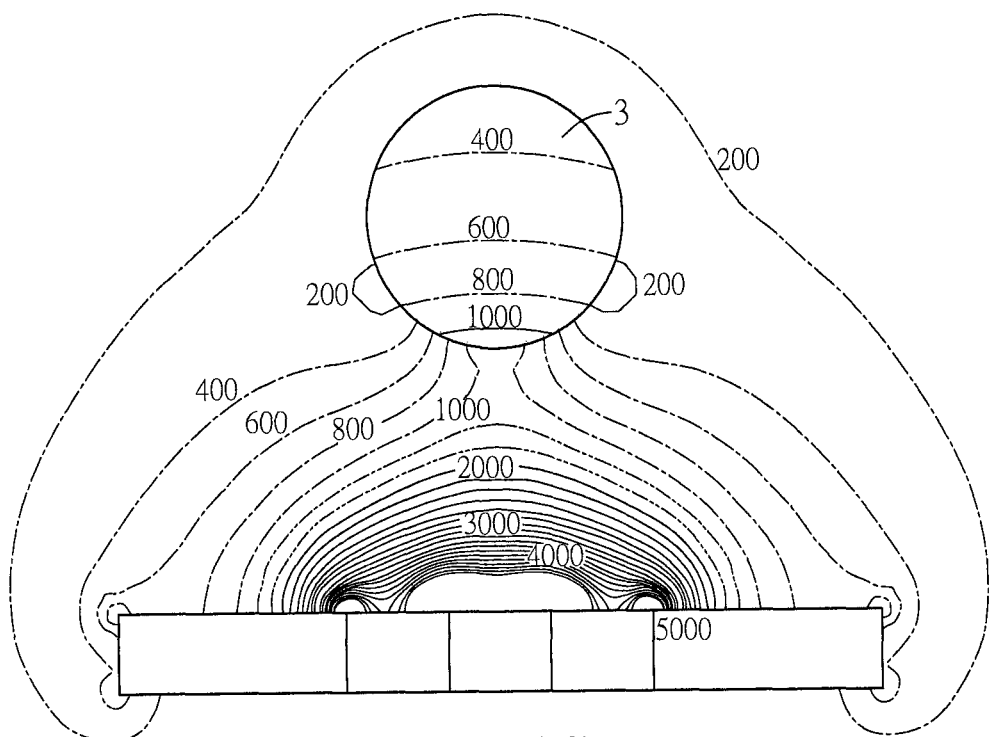

Then, different voltage influences on the space distribution of the field pattern of the electric field are compared. Referring to FIG. 4A to FIG. 4C, the frequency 500 KHz of the constant electrical stimulation signal is applied, and the electrode length a of the first electrode 121 and the second electrode 122, the distance b between the electrodes and the distance c to the target zone to be stimulated are all fixed (a=2 mm, b=2 mm, c=5 mm). Different voltage influences on the space distribution of the field pattern of the electric field are shown in the figures (the voltage is 3V in FIG. 4A, the voltage is 5V in FIG. 4B, the voltage is 10V in FIG. 4C). From the figures, it is seen that as the voltage is greater, the space distribution of the field pattern of the electric field also becomes larger.

Figure 4D:
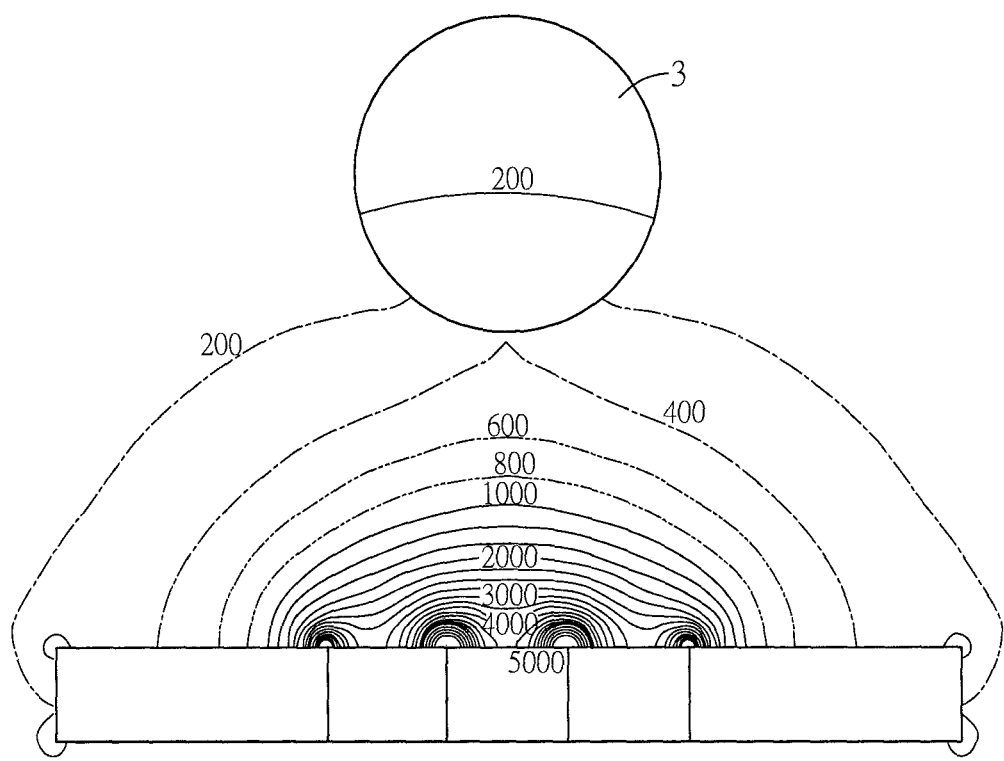
Figure 4E:
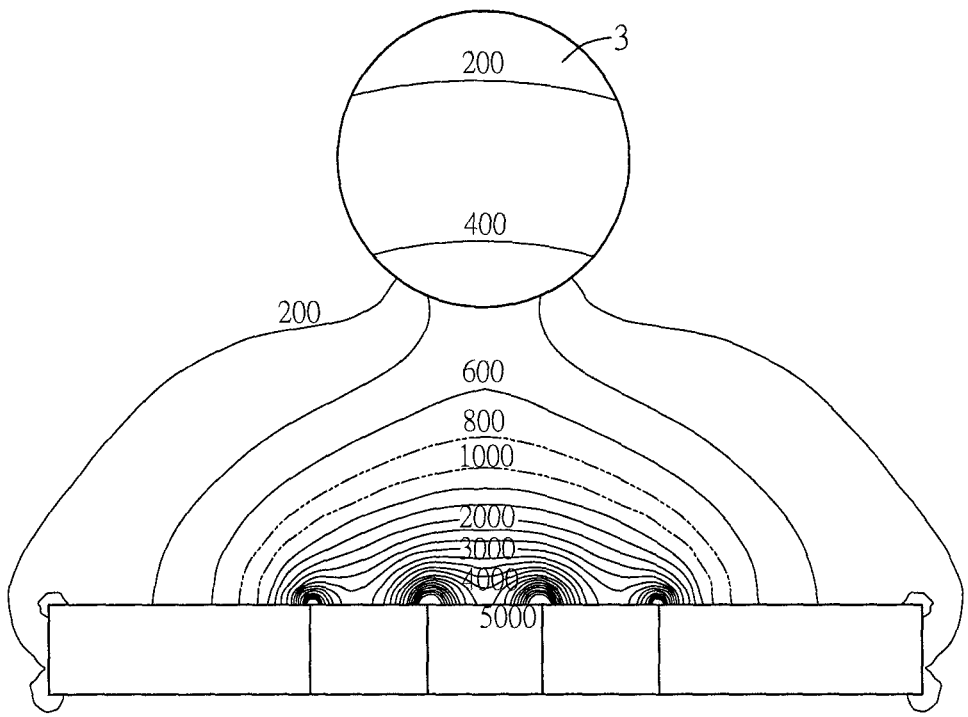

Then, comparing FIG. 4B, FIG. 4D and FIG. 4E, the electrical stimulation signal with 5V is applied, and the electrode length a of the first electrode 121 and the second electrode 122, the distance b between the electrodes, and the distance c to the target zone to be stimulated are all fixed (a=2 mm, b=2 mm, c=5 mm). Different frequency influences of the electrical stimulation signal on the space distribution of the field pattern of the electric field are shown in the figures (the frequency of the electrical stimulation signal is 200 KHz in FIG. 4D, the frequency of the electrical stimulation signal is 500 KHz in FIG. 4B, the frequency of the electrical stimulation signal is 800 KHz in FIG. 4E). From FIG. 5B, because around the arc length at 4 mm it is the point closest to the electrical stimulation unit, the most intensive strength of the electric field is here. As the frequency is increased, the space distribution of the field pattern of the electric field also becomes larger. From FIG. 3A to FIG. 4E, in the embodiment, the electric field strength ranges from 100 V/m to 5000 V/m, preferably from 400 V/m to 5000 V/m.

Figure 5A:
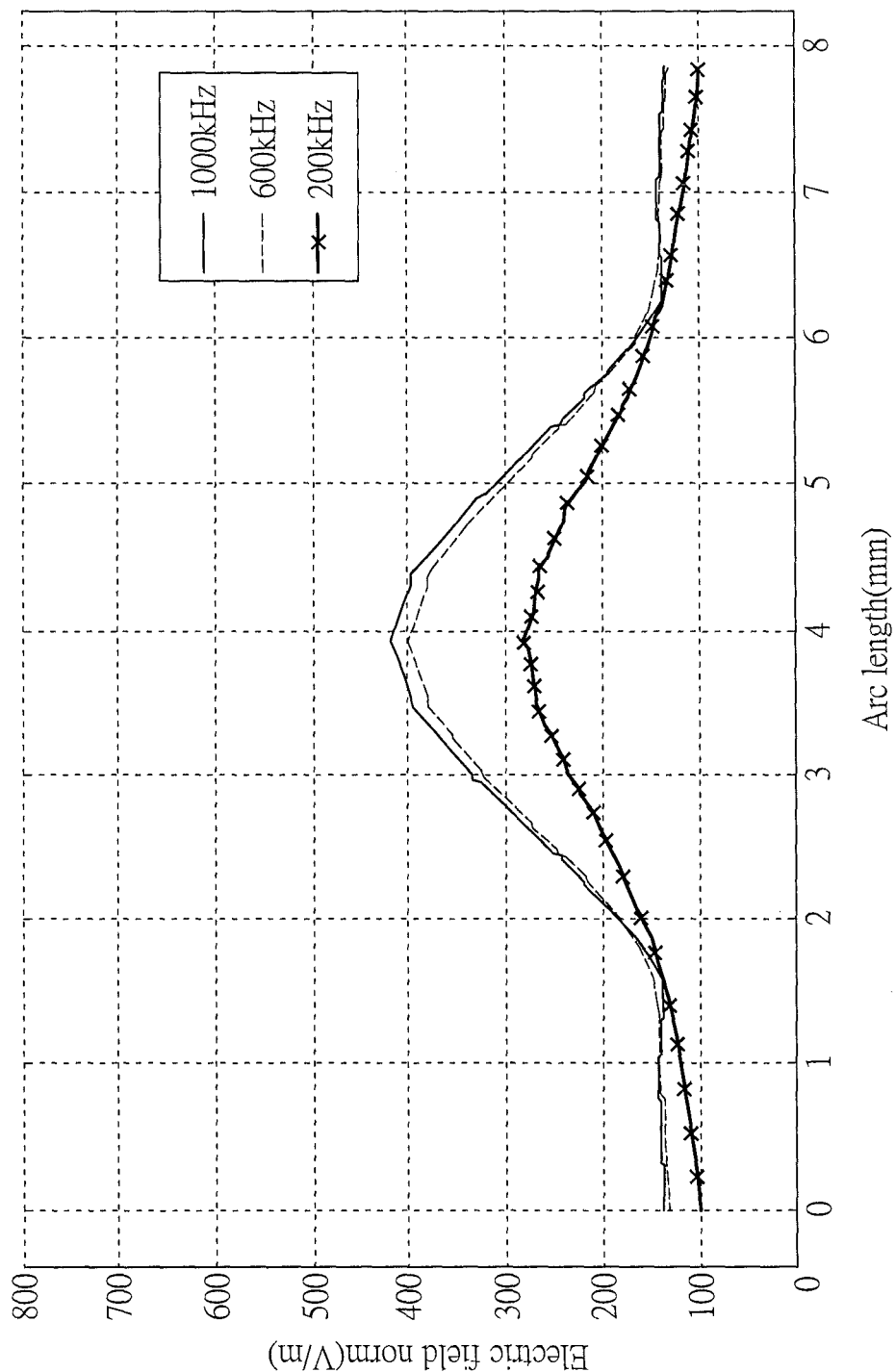
FIG. 5A and FIG. 5B are schematic diagrams of the electric field simulation at the condition that the electrical stimulation device operates at different electrode intervals and different frequencies of the electrical stimulation signals.
Figure 5B:
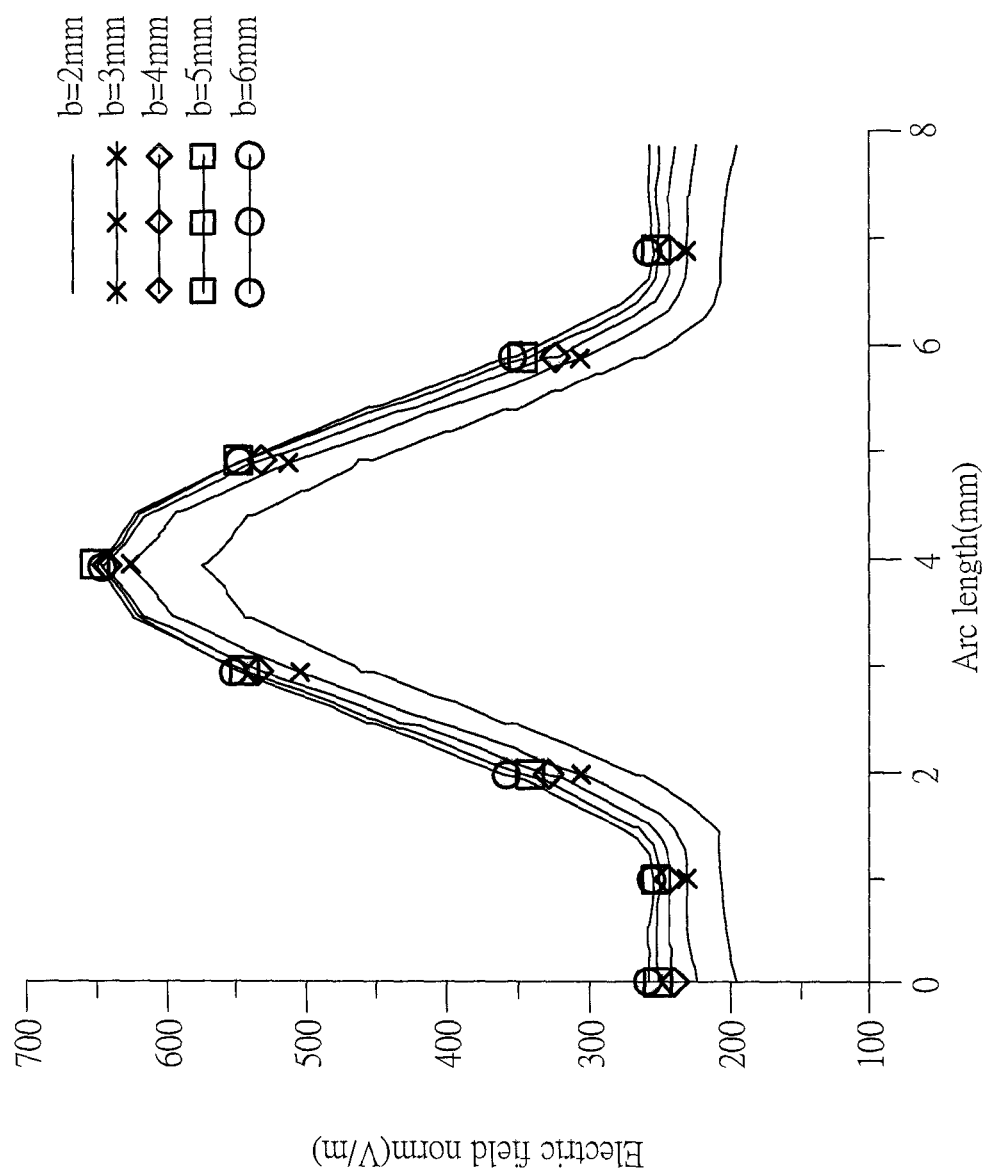

Referring to FIG. 5A and FIG. 5B, the diameter of the target (circular dorsal root ganglion 3) to be stimulated also shown in FIG. 2B is 5 mm, the electrode length a of the first electrode 121 and the second electrode 122 is about 1 mm, the distance c is about 5 mm and the input voltage is 5V. The electric field strength on the target to be stimulated for different arc length location of the electrode (in the horizontal axis, the tangent at the left side of the circle is taken as the start point of the arc 0 mm) is shown in the figures. In FIG. 5A, the corresponding strength of the electric field is detected at different frequencies (200 KHz, 600 KHz and 1000 KHz) for electric stimulation are compared. In FIG. 5B, the corresponding strength of the electric field is detected at different distances b between electrodes (b is 2, 3, 4, 5, or 6 mm.) From FIG. 5A, as the frequency of the electric stimulation signal is increased, the strength of the electric field is more intensive and the space distribution of the field pattern of the electric field also becomes larger. For example, under the condition that the frequency of the electric stimulation signal is 1000 KHz, the maximum strength of the electric field at the target zone may reach 400 V/m. Under the condition that the frequency of the electric stimulation signal is 200 KHz, the maximum strength of the electric field at the target zone may be not intensive enough to reach 300 V/m. From FIG. 5B, if the distance b is between 4 mm~6 mm, the electric field strength of the electromagnetic field reaches its maximum.

After the electrical stimulation unit 12 is implanted in the organism, to utilize it as fully as possible, the electrical stimulation device 1 of the embodiment is able to operate in a low-frequency mode to assist the doctor in checking whether the electrodes are at correct positions after the implantation. For example, in the low-frequency mode, the electrical stimulation unit 12 may, according to the control of the first control unit 11, deliver a second electrical stimulation signal of which the frequency is between 0.1 Hz~1 KHz and its pulse width is between 10 μs~500 μs. The electrical stimulation unit 12 delivers the second electrical stimulation signal to detect the corresponding spasm of the muscle so as to check whether the implanted electrical stimulation unit is loose or at wrong positions.

Figure 6:
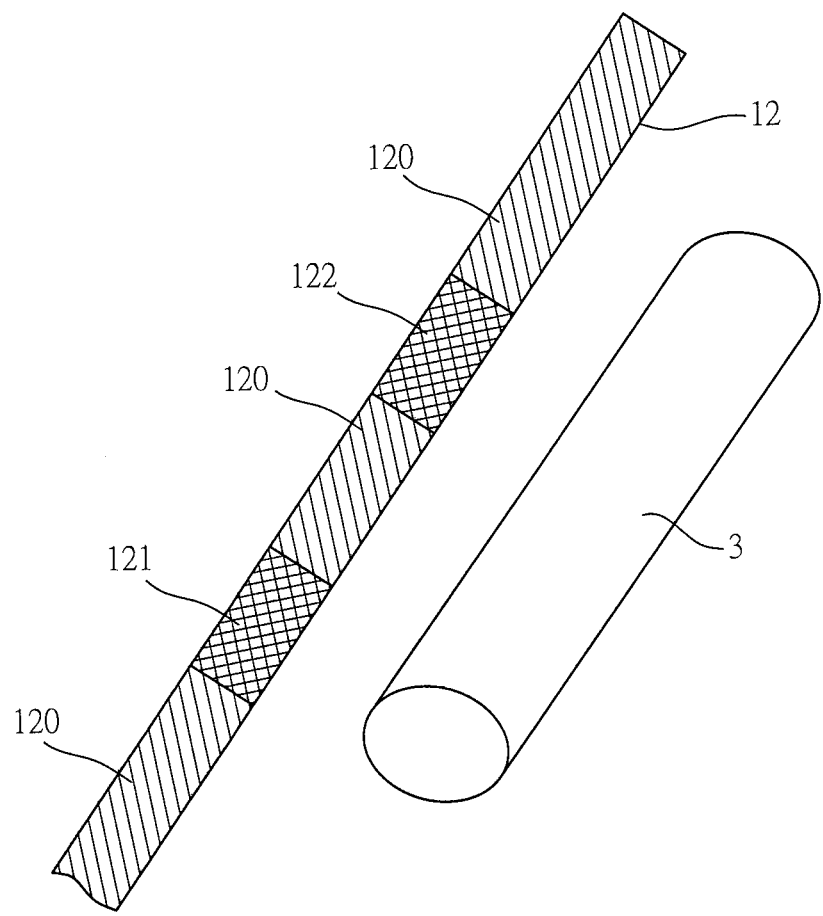
FIG. 6 is another schematic diagram showing the electrical stimulation device in FIG. 1A.

Referring to FIG. 2A and FIG. 6, in the embodiment, the electrical stimulation unit 12 is like a straight line, but it is not limited thereto. The shape of the electrical stimulation unit 12 may be like the shape described in the following embodiments, but it is not limited thereto.

In the embodiment, the electrical stimulation device 1 is an active electrical stimulation device of which the first control unit 11 together with the electrical stimulation unit 12 are implanted in the target zone of the organism. In other words, both the first control unit 11 and the electrical stimulation unit 12 are implanted in the organism subcutaneously. Alternatively, the first control unit 11 and the electrical stimulation unit 12 are integrated into one part first and then implanted subcutaneously. Because of electrically coupled to the controller 2 outside the organism, the first control unit 11 can receive the parameter signal and energy from the second control unit 21 so the electrical stimulation unit 12 may electrically stimulate the target zone of the organism.

Figure 7:
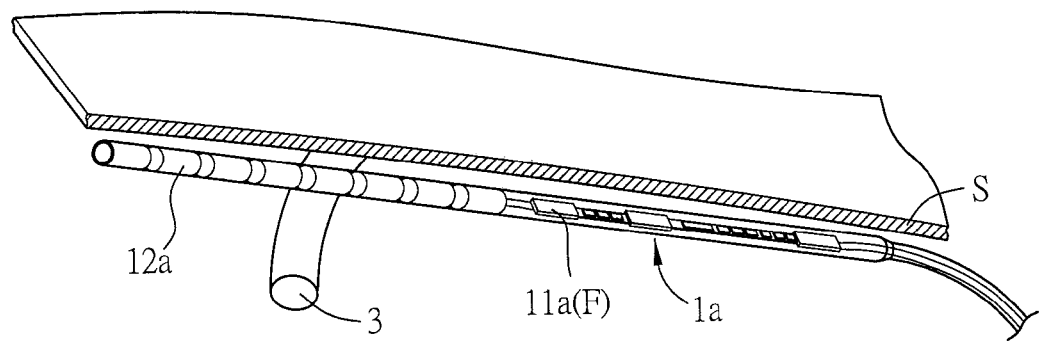
FIG. 7 and FIG. 8 are schematic diagrams showing another examples of the electrical stimulation device according to other embodiments.

The electrical stimulation device of the disclosure is not limited to the electrical stimulation device 1 mentioned above. In other embodiment, the active electrical stimulation device may be like the electrical stimulation device in FIG. 7. The electrical stimulation device 1a in the embodiment and the electrical stimulation device 1 in the previous embodiment have substantially alike elements thereof, and the first control unit 11a and the electrical stimulation unit 12a are also respectively implanted in the epidermis S of the organism (subcutaneous). However in the embodiment, the first control unit 11a of the electrical stimulation device 1a is a FPCB (flexible printed circuit board) integrated in the electrical stimulation unit, and it still can receive the parameter signal and electrical energy from the second control unit (not shown in the figure) outside the organism, and deliver the electrical stimulation signal to the electrical stimulation unit 12a to electrically stimulate the dorsal root ganglion 3 of the organism. In the embodiment, the electrical stimulation device 1a may be narrowed enough to be implanted subcutaneously for abating the burden of the organism (or the patient).

Figure 8:
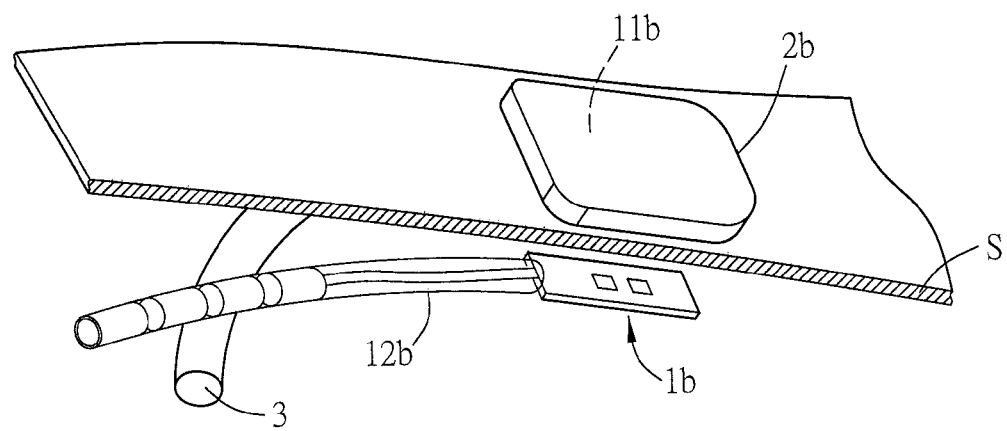

Alternatively, the electrical stimulation device may be like the device shown in FIG. 8. Referring to FIG. 8, in the embodiment, the electrical stimulation device 1b is a passive electrical stimulation device. However, the first control unit 11b of the electrical stimulation device 1b is integrated in the controller 2 outside the epidermis S of the organism (subcutaneous). Thus, the implanted electrical stimulation device 1b does not contain the control unit therein. The electrical stimulation unit 11b (lead) at its end has a FPCB which is implanted subcutaneously and not deeply (for example the depth is less than 5 cm). The controller 2b which is not implanted within the skin can deliver an electrical stimulation signal to the electrical stimulation unit 11b, so the electrical stimulation unit 12b can electrically stimulate the dorsal root ganglion 3 of the organism.

Figure 9:
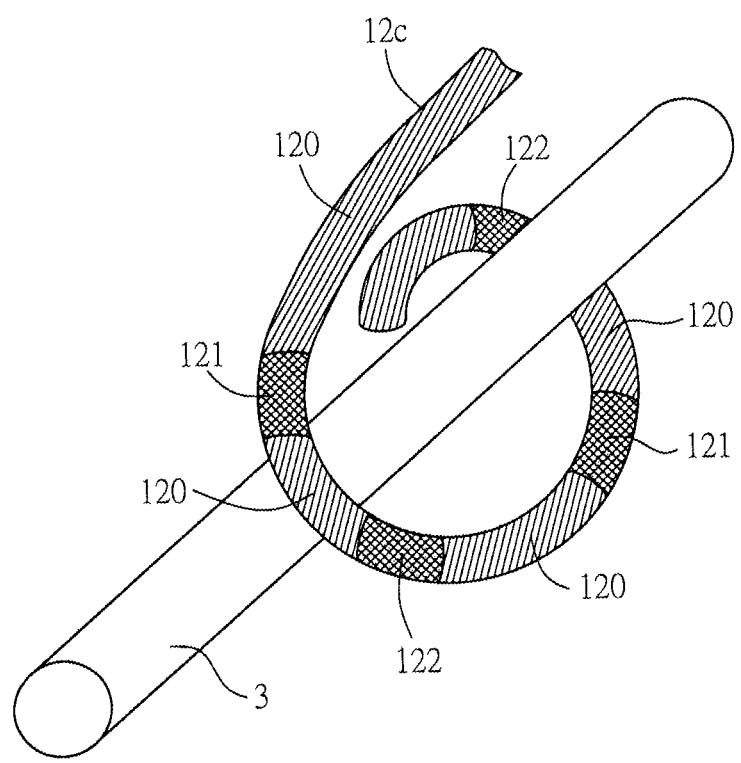
FIG. 9 to FIG. 14 are schematic diagrams showing another examples of the electrical stimulation device.
Figure 12:
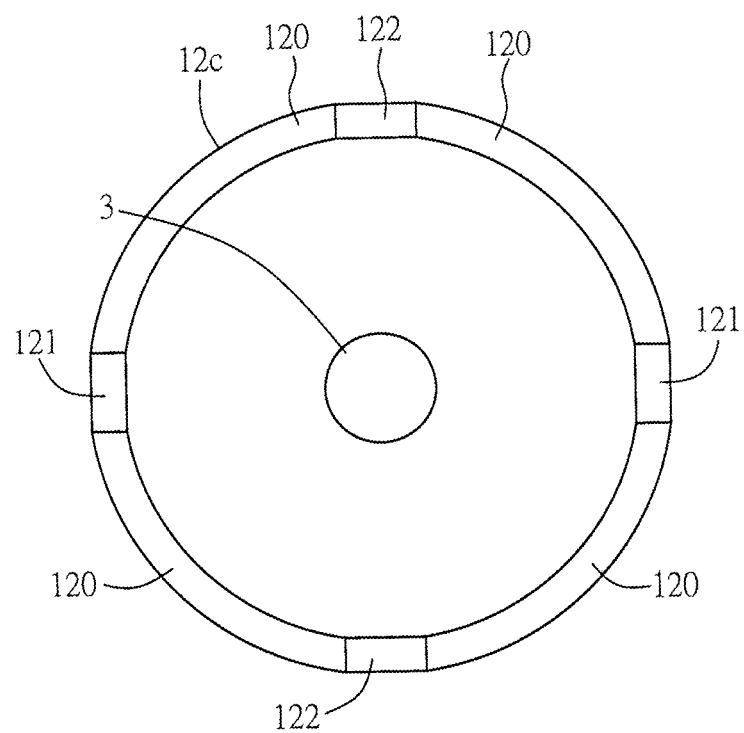
Figure 13:
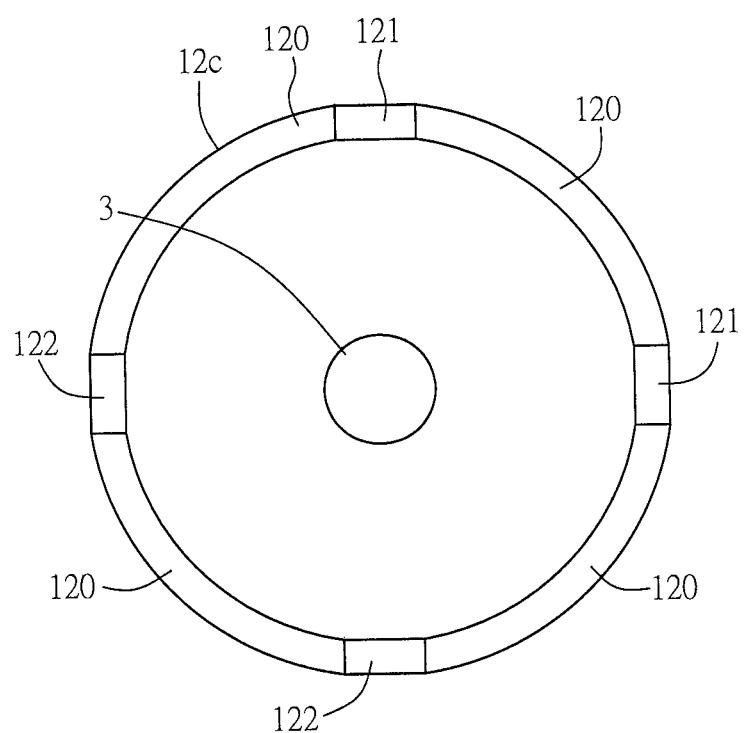
Figure 14:
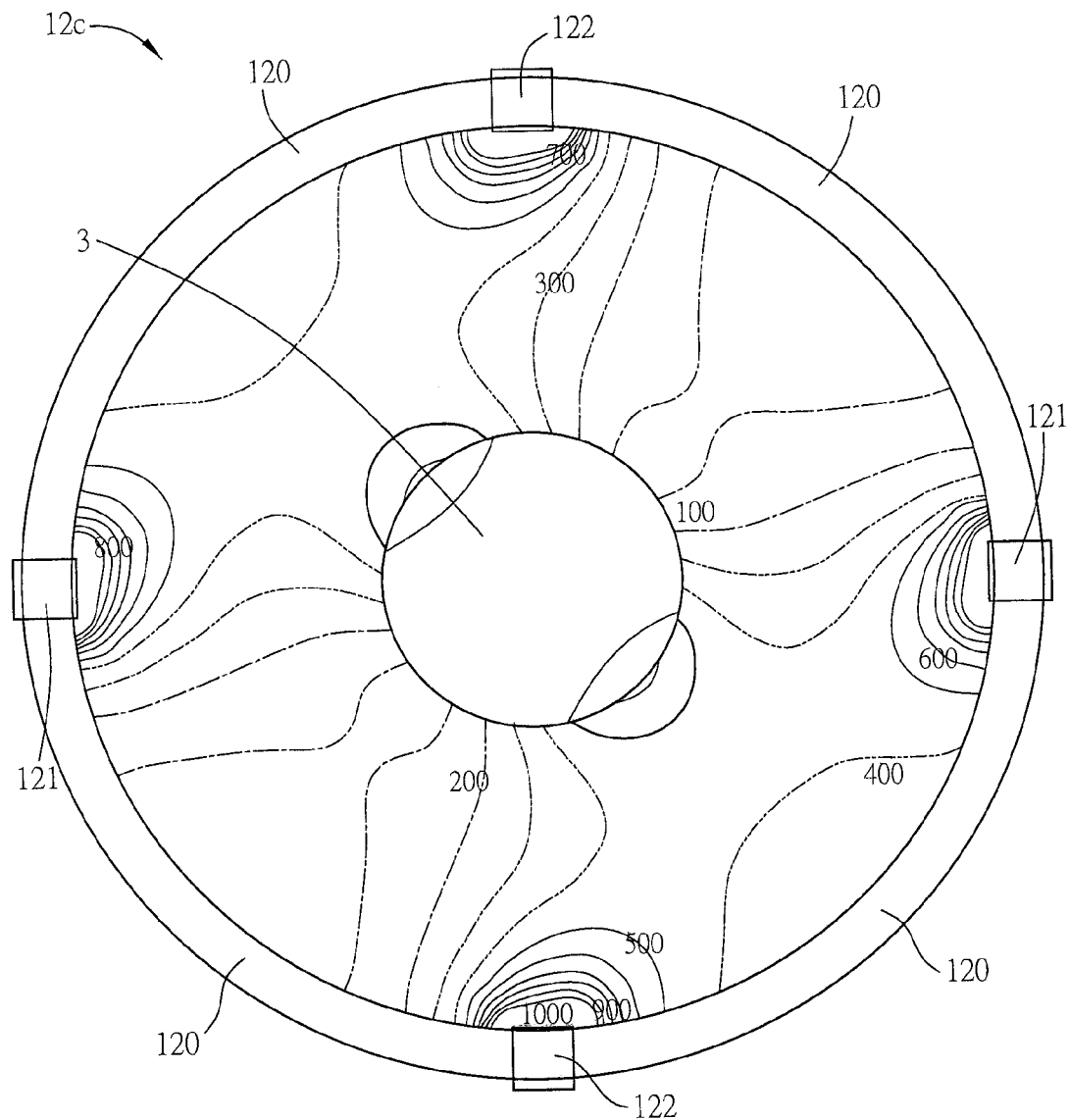

As to implementation of the electrical stimulation unit, it is not limited to the above electrical stimulation unit 12. FIGS. 9, 12, 13 illustrate another embodiment. In the embodiment, the electrical stimulation unit 12c is like a ring, and the electrical stimulation unit 12c includes at least two first electrodes 121 and at least two second electrodes 122. The first electrodes 121 and the second electrode 122 are interlaced at intervals (as shown in FIG. 12). Alternatively, the first electrodes 121 and the second electrodes 122 may be arranged sequentially without interlacement (as shown in FIG. 13). The electric field generated by the first electrode 121 and the second electrode 122 of the electrical stimulation unit 12 surrounds and covers the target dorsal root ganglion 3 (as shown in FIG. 14) to stimulate it with low intensity, low temperature and high-frequency electromagnetism. Furthermore, if the position is closer to the first electrode 121 and the second electrode 122, the electric field is more intensive.

Figure 10:
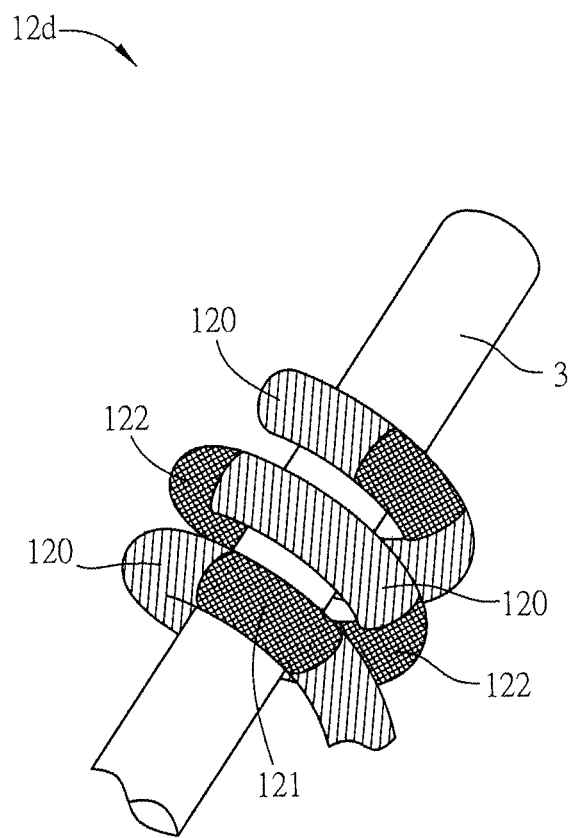

Referring to FIG. 10, the electrical stimulation unit 12d may be like a helix, and the electrical stimulation unit 12d includes at least two first electrodes 121 and at least two second electrodes 122. In the embodiment, the electrical stimulation unit 12d includes two first electrodes 121 and two second electrodes 122 for example. The arrangement of the first electrode 121 and the second electrode 122 is not limited. The first electrodes 121 and the second electrodes 122 may be interlaced or arranged without interlacement, and the first electrodes 121 and the second electrodes 122 may be arranged like a helix to surround the dorsal root ganglion 3. Because the electric field generated by the first electrodes 121 and the second electrodes 122 like a helix surround and cover the target dorsal root ganglion 3, the target dorsal root ganglion 3 is electrically stimulated with low intensity, low temperature and high frequency.

Figure 11:
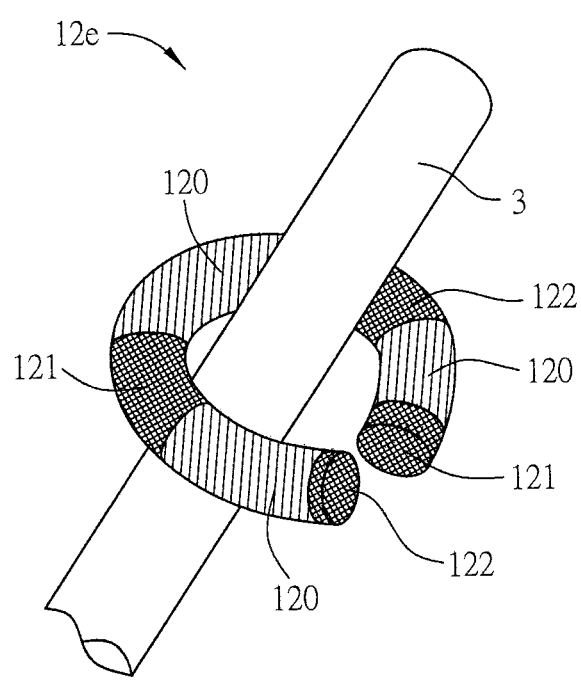

Referring to FIG. 11, in the embodiment, the electrical stimulation unit 12e is like an arc, and the electrical stimulation unit 12e includes at least two first electrodes 121 and at least two second electrodes 122. In the embodiment, the electrical stimulation unit 12e includes two first electrodes 121 and two second electrodes 122 for example. The arrangement of the first electrodes 121 and the second electrodes 122 is not limited. The first electrodes 121 and the second electrodes 122 may be interlaced or arranged without interlacement, and the first electrodes 121 and the second electrodes 122 may be arranged to surround the dorsal root ganglion 3. Because the electric field generated by the first electrode 121 and the second electrode 122 surround and cover the dorsal root ganglion 3, the target dorsal root ganglion 3 is stimulated with low intensity, low temperature and high frequency.

Figure 15:
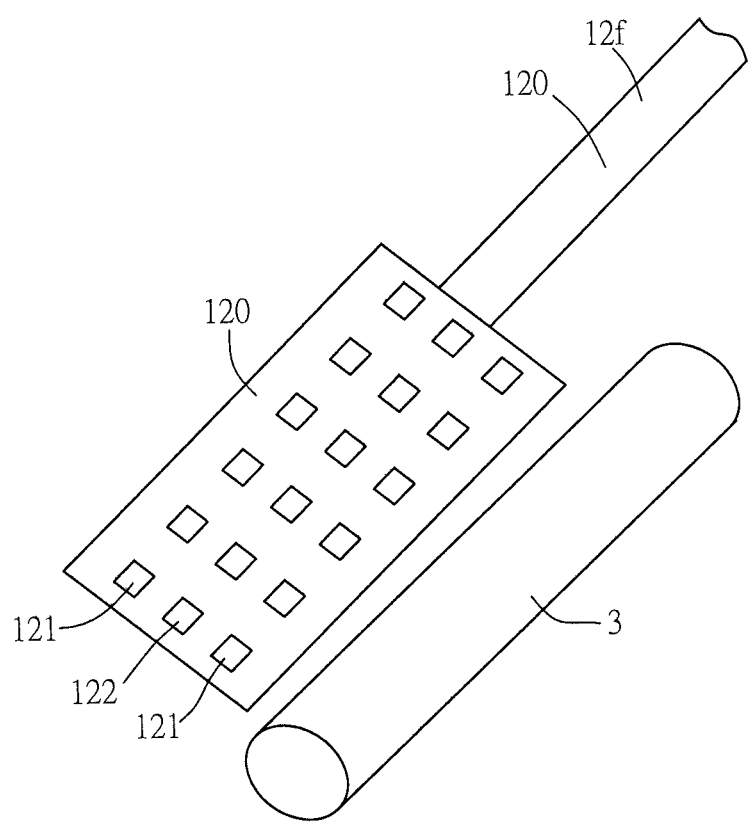
FIG. 15 is a schematic diagram showing the application of the electrical stimulation device according to another embodiment.

Referring to FIG. 15, in the embodiment, the electrical stimulation unit 12f is like a flake (or a flat), and the electrical stimulation unit 12f includes a plurality of the first electrodes 121 and a plurality of the second electrodes 122. These first electrodes 121 and these second electrodes 122 are arranged at intervals in an array. Similarly, the electric field generated by the first electrode 121 and the second electrode 122 surrounds and covers the dorsal root ganglion 3 so as to electrically stimulate the target, the dorsal root ganglion 3, with low intensity and low temperature.

In addition to being applied for pain-management or pain-reducing as described above, the present invention also provides several embodiments, such as the electrical stimulation device, method, and computer-readable medium, which are applied for reducing spasticity.

Figure 16:
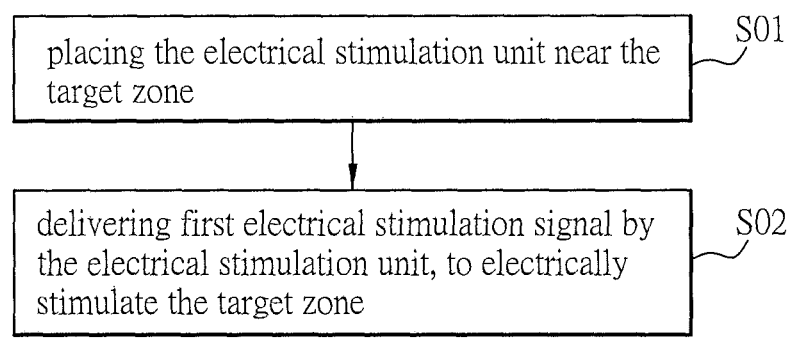
FIG. 16 is a flow chart showing the application of method for reducing spasticity according to another embodiment.

Please refer to FIG. 16, which is a flow chart showing the application of method for reducing spasticity according to another embodiment of the present invention.

In the present embodiment, the method for reducing spasticity is applied to electrically stimulate a target zone of an organism by the electrical stimulation device described above. As described above, the electrical stimulation device 1 includes at least an electrical stimulation unit 11 and the electrical stimulation unit 11 includes at least a first electrode 111 and a second electrode 112. The method comprises the following steps: placing the electrical stimulation unit 11 near the target zone (Step S01); and delivering a first electrical stimulation signal by the electrical stimulation unit 11 to electrically stimulate the target zone (Step S02). Accordingly, an electric field covering the target zone is generated between the first electrode 111 and the second electrode 112 according to the first electrical stimulation signal, and the strength of the electric field ranges from 100 V/m to 1000 V/m.

In other words, the process utilizing the electrical stimulation device for electrically stimulating a target zone of an organism to reducing spastic symptoms of such organism can also be described as followed:

A spasticity management method of an electrical stimulation device comprising the following steps. First, positioning the electrical stimulation device 1, which is at least at a distance c away from a nerve of a target zone. The distance c is a minimum linear distance between the electrical stimulation device 1 and the targeted nerve, and the distance c is no more than 10 mm. Second, applying a preset voltage to the first and second electrodes (i.e., the positive and negative electrodes) so that an electric field covering and stimulating the nerve is produced between the positive and negative electrodes.

In addition, suitable parameters of the preset voltage (such as the voltage ranges, frequency ranges, PRF ranges, and pulse width) and the suitable strength of the electric field is substantially the same as those of first electrical stimulation signal and the electric field generated accordingly as described above, and they are not repeated here.

The method according to the present embodiment can effectively reduce the spastic symptoms and also can reduce such symptoms for a long time. Unlike the treatment of medicines, the spastic symptoms can be reduced after electrically stimulated for only 5 minutes according to the method of the present embodiment. The organism can receive the electrical stimulation for a second time at 24 hours after the first time of the electrical stimulation for maintaining the effect of spasticity amelioration. The time interval between the two electrical stimulations can be as long as 2, 4, 6, 8, 10, 12, 14, 16, 18, 20, or 22 hours, or 1, 2, 3, 4, 5, 6, 7, 8, 9, 10, 11, 12, 13 or 14 days, and the spastic symptoms are still reduced. Therefore, the organism may not have to receive the electrical stimulation once or even several times a day to reduce the spastic symptoms. The details are described in the following experiments and are omitted here.

Because configuration, variation or connection relationship to other elements of each detail elements of the electrical stimulation device 1, as well as other variations of the method of the present embodiment, can refer to the previous embodiments, they are not repeated here.

Moreover, the present disclosure also provides another embodiment, which is described as followed. In a neurostimulation method, the improvement of such method consists of, or comprises, using the electrical stimulation device 1 which is configured to deliver a first electrical stimulation signal to a target zone (which can be a nerve or a ganglion) of an organism to electrically stimulate the target zone to treat spasticity of an organism. According to the first electrical stimulation signal, an electric field covering the target zone is generated between the first electrode 111 and the second electrode 112 of the electrical stimulation device 1. The strength of the electric field ranges from 100 V/m to 1000 V/m.

Because configuration, variation or connection relationship to other elements of each detail elements of the electrical stimulation device 1, as well as other variations of the method of the present embodiment, can refer to the previous embodiments, they are not repeated here.

Figure 17A:
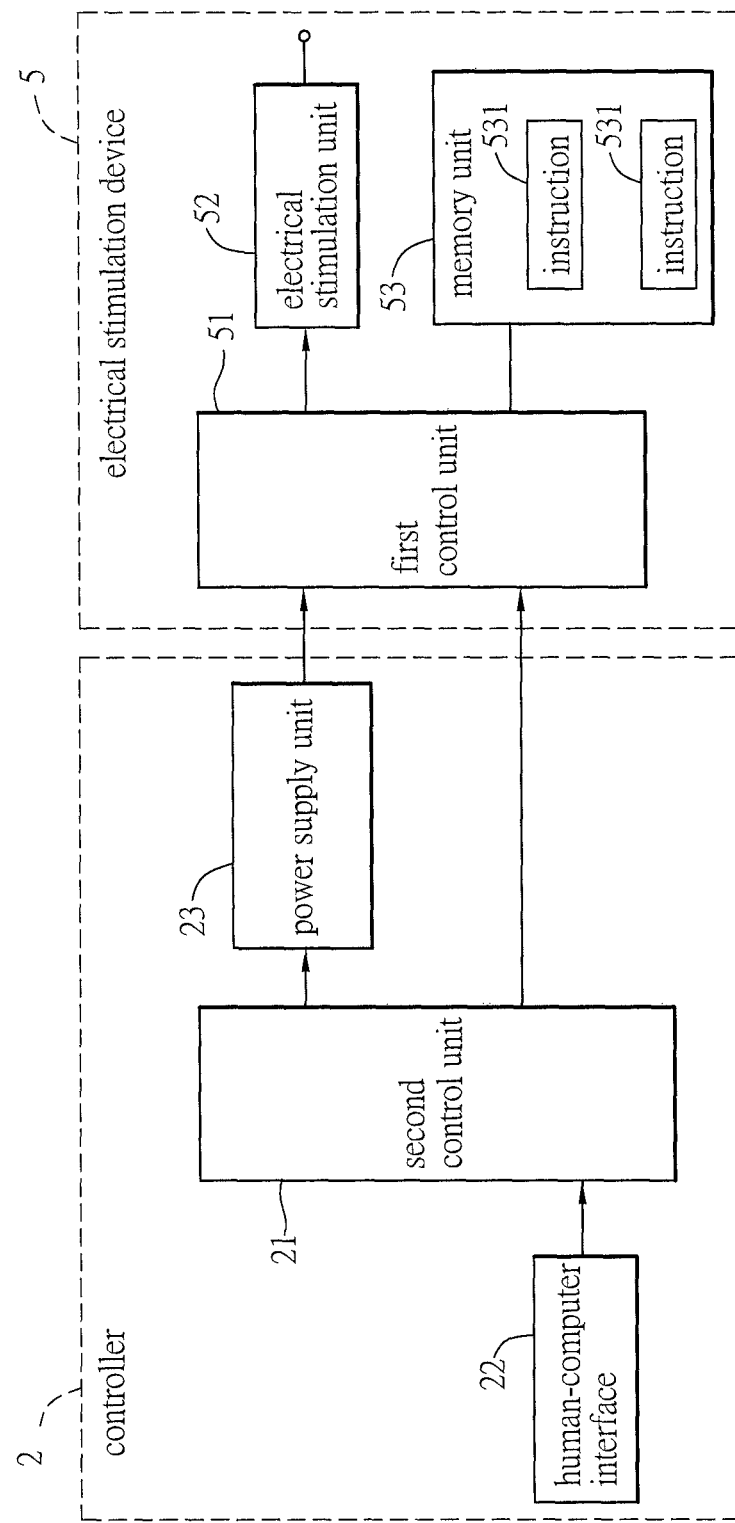
FIG. 17A is a functional block diagram showing the computer-readable medium according to another embodiment.

A computer-readable medium according to still another embodiment of the present invention is also provided. FIG. 17A is a functional block diagram showing the computer-readable medium according to another embodiment, and FIG. 17B is a flow chart showing the process executed by the computer-readable medium according to another embodiment.

The electrical stimulation device 5 also includes a first control unit 51 and an electrical stimulation unit 52. The electrical stimulation unit 52 electrically couples to the first control unit 51. The electrical stimulation device 5 is similar to the electrical stimulation device 1 as described above. The configuration, variation or connection relationship to other elements of each detail elements of the electrical stimulation device 5, as well as the connection relationship to the controller 2, are also substantially the same as those of the electrical stimulation device 1. On the other hand, first control unit 51 further electrically couples to a computer-readable medium, which is exemplified as the memory unit 53 in the present embodiment. The memory unit 53 is a non-transitory storage medium, and can be a memory, a memory card, an optical disc drive, a video tape drive, a magnetic tape drive, and/or the combination thereof. The memory can be a ROM, Flash Memory, or Field-Programmable Gate Array (FPGA), or other non-transitory memory.

One or more instructions 531 are stored in the memory unit 53. For the clarity of the figures, two instructions 531 are stored in the memory unit 53 as shown in FIG. 17A, but the present invention is not limited thereto. The first control unit 51 can assess the instructions 531 from the memory unit 53, and execute the t instructions 531 to control the action of the electrical stimulation device 5. The electrical stimulation device 5 can be applied to electrically stimulate a target zone of an organism for ameliorating the spastic symptoms of the organism. The electrical stimulation unit 52 also comprises a first electrode and second electrode.

The instructions 531 are executed by the first control unit 51 to cause the electrical stimulation device 5 to execute an electrical stimulation process for reducing spasticity, which comprises the following steps: delivering a first electrical stimulation signal by the electrical stimulation unit 52 to electrically stimulate the target zone (Step S11). During the process of the electrical stimulation, an electric field covering the target zone is generated between the first electrode and the second electrode according to the first electrical stimulation signal, and a strength of the electric field ranges from 100 V/m to 1000 V/m.

As described above, the present embodiment is exemplified with the electrical stimulation device 5 which is controlled by the first control unit 51 to execute the instructions 531 stored in the memory unit 53 electrically coupled to the first control unit 51. In other words, the electrical stimulation device 5 can independently execute every steps of the electrical stimulation process for reducing spasticity without any external controller.

In other practicing modes, the computer-readable medium of the present embodiment can be electrically coupled to an external controller (e.g., the controller 2) or a control unit or a CPU of the external controller (e.g., the control unit 21 of the controller 2), to make the electrical stimulation device 5 to execute the steps of the electrical stimulation process for reducing spasticity. In such practicing mode, the instructions 531 are assessed by the control unit of the external controller to control the electrical stimulation device 5 to deliver the first electrical stimulation signal. In other words, the electrical stimulation device 5 and the external controller can be seen as a system, which can execute the instructions stored in the computer-readable medium and the steps of the electrical stimulation process for reducing spasticity.

Other technical features of the computer-readable medium of the present embodiment can be referred to relevant description of the electrical stimulation device and the controller as described in the above-mentioned embodiments, and they are not repeated here.

From the below experiments, the operation and effect of the electrical stimulation device which stimulates the dorsal root ganglion and for applied for reducing spastic symptoms are explained. However, the below examples are just explanatory but not limited to the scope of the invention.

Experimental Example 1: The Pain Behavior Test on the Foot in the Rat—Von Frey (VF) Test Sprague-Dawley rats (SD rats) of about 275-350 grams weight are used (BioLASCO, Taiwan co., Ltd., Taiwan) and they are provided from the central laboratory animal center of Shin Kong Wu Ho-Su Memorial Hospital. The spinal nerve ligation (SNL) is performed on the L5 spinal nerve of the SD rat. After the development of the pain behavior is stable for few days and conforms to the clinical pain development model, the electronic stimulation unit 1 is implanted and then the electrical stimulation therapy is performed. In this experimental example, the rats are divided into the control group and the experimental group according to the different electrical stimulation treatments. As to the experimental group, the pain behavior is continuously observed for 7 days after surgery. After the pain behavior is stable, the electrical stimulation therapy is performed for 5 minutes once a week totally three times (FIG. 18A), or biweekly totally two times (FIG. 18B, and the responses to the pain behavior tests are observed. The results are shown in FIGS. 18A and 18B.

Figure 18A:
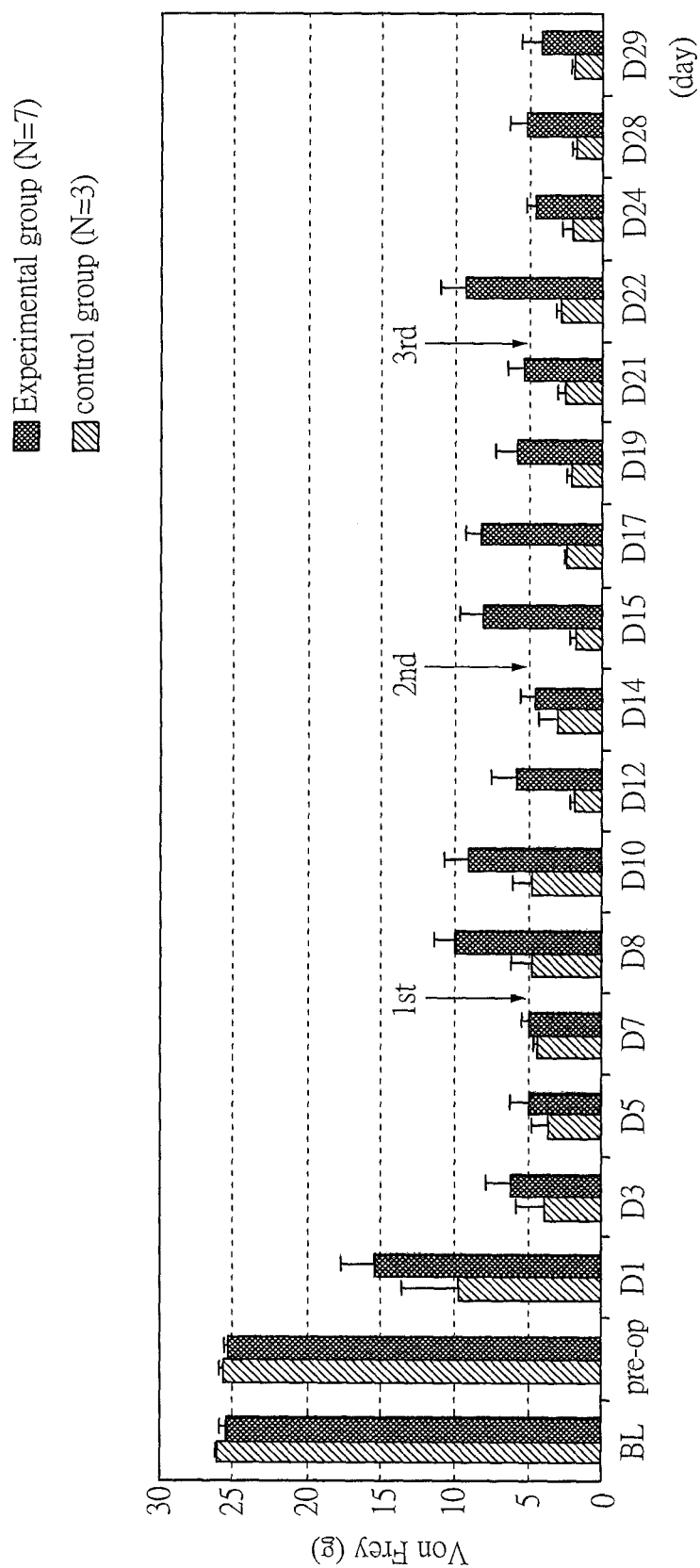
FIGS. 18A and 18B are the results of the pain behavior test on the foot in the rat—Von Frey (VF) according to Experimental example 1.

As shown in FIG. 18A, the pain behavior of the control group (N=3) becomes stable on the third day until the 29th day, and Von Frey pain pressure thresholds are all less than 5 g (between 1.72±0.39 g and 4.85±1.31 g). As to the experimental group (N=7), its pain behavior is similar to that of the control group before receiving electrical stimulation therapy (on the 7th day, D7) and becomes stable on about the third day similarly. However, after receiving the first (D7) electrical stimulation, its Von Frey pain pressure thresholds are improved. They are different from the control group (D8: 4.73±1.47 g; D10: 4.85±1.31 g) both on D8 (9.85±1.56 g) and D10 (9.0±1.68 g), the tolerance levels of the pressure thresholds in the experimental group are improved up to about 10 g, the pain pressure thresholds increase to about 2.08 times as compared with the control group, and the pain relief will gradually decay until receiving the second electrical stimulation therapy (the experimental group D14: 4.53±1.08 g; the control group D14: 2.98±1.44 g). On the next day after receiving the second (D14) electrical stimulation therapy (the experimental group D15: 8.12±1.65 g; the control group D15: 1.81±0.53 g; the pain pressure threshold of the experimental group is about 4.49 times greater than that of the control group), the therapy of receiving the first electrical stimulation is still effective. The response to the pain behavior test is still excellent on the next day after receiving the third (D21) electrical stimulation therapy (the experimental group D22: 9.17±1.93 g; the control group D22: 2.73±0.57 g; the pain pressure threshold of the experimental group is about 3.36 times greater than that of the control group). Obviously, the pain can be immediately relieved, and there are differences of the pain pressure thresholds between the experimental group and the control group every time after receiving the electrical stimulation therapy. It approves that after the electrical stimulation unit of the invention is implanted, receiving the electrical stimulation therapy for 5 minutes once a week can relieve the pain for a short time.

Figure 18B:
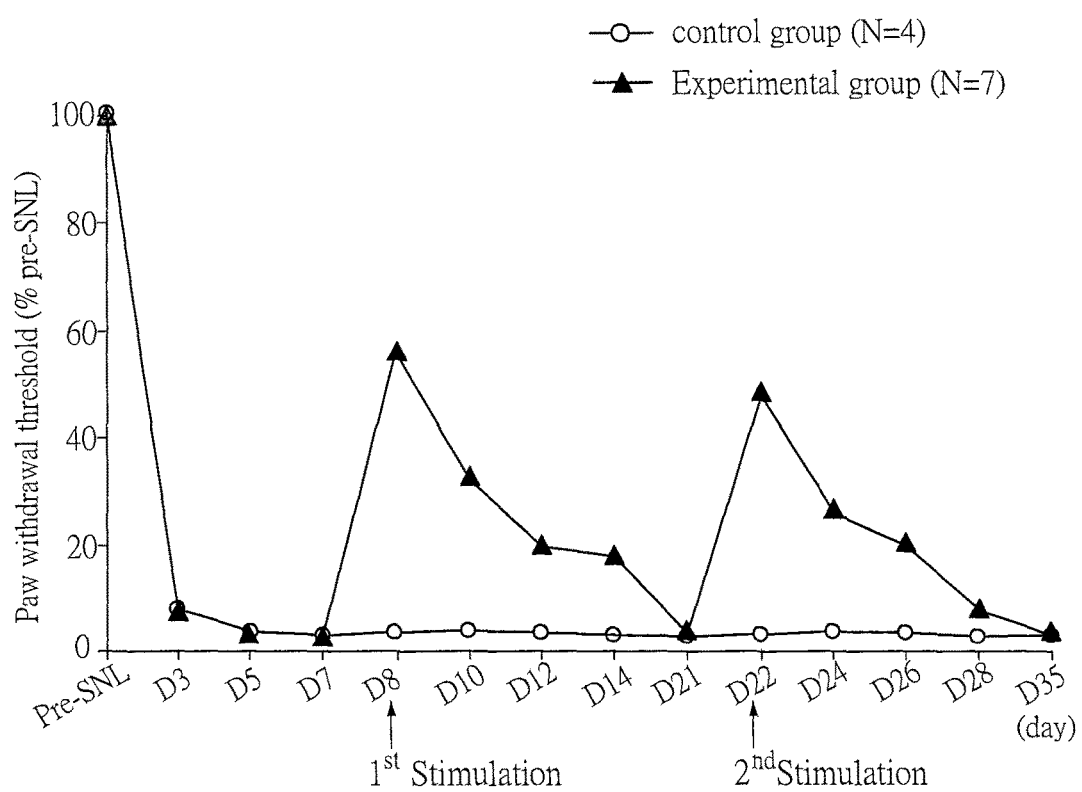

In FIG. 18B, pain behaviors of the control group (N=4) and the experimental group (N=7) are shown as percent of paw withdrawal threshold of prespinal nerve ligation baseline (Pre-SNL) at different time points. Similarly, both of the experimental group and the control group, pain behaviors become stable on about the third day before receiving the first electrical stimulation treatment. The pain behavior of the control group remain stable on the third day until the 35th day. However, after receiving the first electrical stimulation, its paw withdrawal thresholds are significantly improved (D8: about 58%) and gradually decayed, but remain effective, on D10 to D14 (D10: about 35%; D12: about 20%; D14: about 18%) when compared with the control group. The paw withdrawal thresholds of the experimental group returned to pre-stimulation level at 14 days (D21) after the first electrical stimulation. After receiving the second electrical stimulation therapy, the paw withdrawal thresholds of the experimental group are again significantly improved (D22: about 48%) and gradually decayed but remain effective on D24 to D28 (D24: about 25%; D26: about 20%; D28: about 8%).

Figure 22:
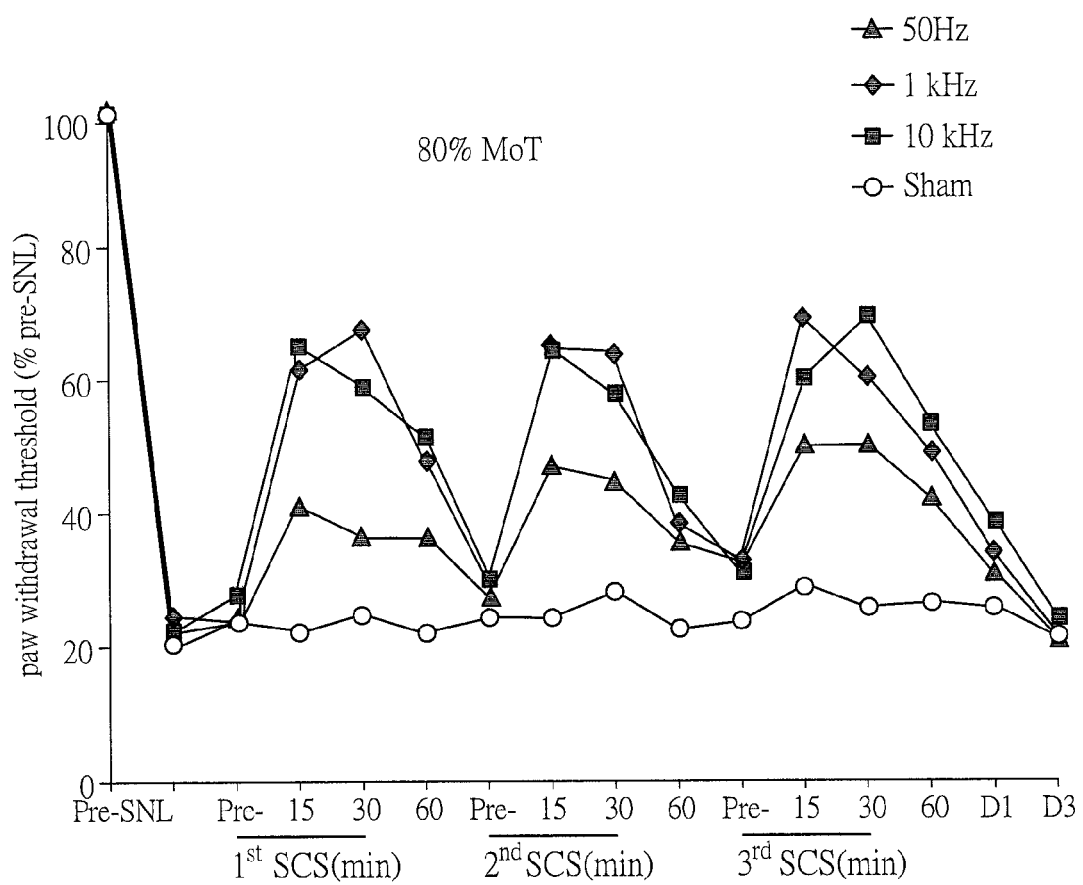
FIG. 22 is the paw withdrawal threshold results of the SCI rats of neuropathic pain after treated with the conventional electrical stimulation.

In addition, as shown in FIG. 22 of the results demonstrated by Ronen Shechter et al. (Ronen Shechter et al. (2013, August), Conventional and Kilohertz-frequency Spinal Cord Stimulation Produces Intensity- and Frequency-dependent Inhibition of Mechanical Hypersensitivity in a Rat Model of Neuropathic Pain, ANESTHESIOLOGY, 119 (2), 422-32), which also uses the same animal model (SD rats receiving SNL to mimic neuropathic pain) as the present experimental example, the effect of the electrical stimulation (i.e., the paw withdrawal threshold, also represented as percent of pre-SNL baseline) of 50 Hz, 1 kHz, and 10 kHz of Ronen Shechter et al. started to drop at 30 minutes after the first time of electrical stimulation, and on the next day of the first electrical stimulation, the effect of the electrical stimulation of 50 Hz, 1 kHz, and 10 kHz of Ronen Shechter et al. further dropped and almost became the same the level of sham group. Moreover, even after receiving electrical stimulations on three consecutive days (once per day), the paw withdrawal threshold of Ronen Shechter et al. still returned to pre-stimulation level at 5 days after the third electrical stimulation. However, according to the results as shown in FIG. 18B, with only one shot of the electrical stimulation of the present embodiment, the effect of pain relief did not reduced until 24 hours after the electrical stimulation. In other words, the effect of the electrical stimulation provided by the present embodiment can last at least for 24 hours, and even for 7 days, or even up to 14 days, after receiving the electrical stimulation. Obviously, the pain can be effectively relived by the PRF electrical stimulation of the present embodiment with a prolonged effect.

Experimental Example 2: Neuroelectrophysiological Test

SD rats are divided into the experimental group and the control group, the experimental group (FIG. 19B) receives the electrical stimulation for 5 minutes, and the control group (FIG. 19A) does not receive any electrical stimulation. The two groups receive large current stimulation (2.5T, C response threshold) on the sciatic nerve under the same conditions so as to induce obvious A responses (referring to A-fiber) and C responses (referring to C-fiber) occurring in the ipsilateral spinal dorsal horn. Before the interventional measure (electrical stimulation for 5 minutes or suspending recording for 5 minutes), the baseline is measured for 30 minutes (18 samples, 100 seconds interval) in advance. After the interventional measure is provided, the large current stimulation is performed on the sciatic nerve once every 30 minutes, the data are continuously recorded for 2 hours, and 5 experimental waveforms are respectively generated in two groups. The results of the control group and the experimental group are respectively shown in FIG. 19A and FIG. 19B.

Figure 19A:
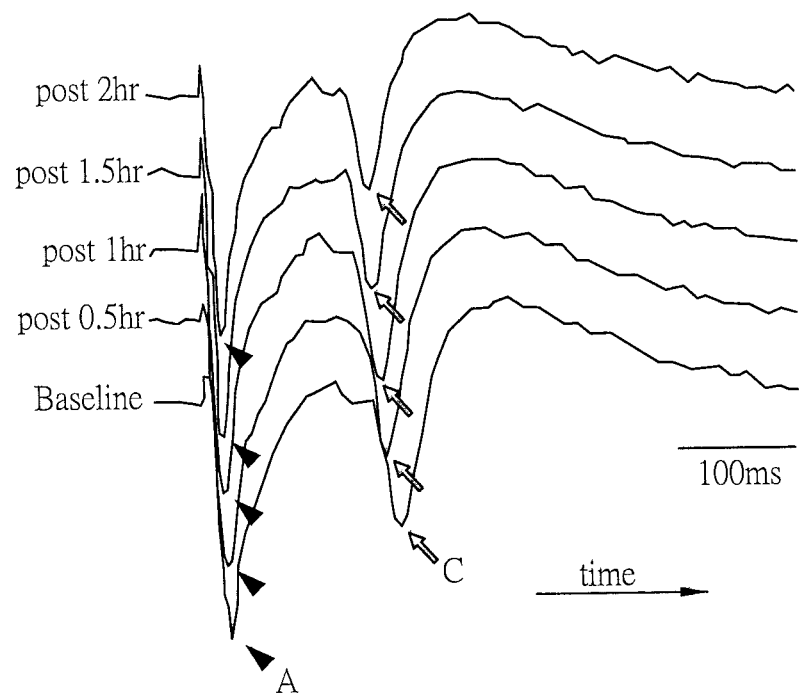
FIGS. 19A and 19B are respectively the results of the control group and the experimental group of the neuroelectrophysiological test according to Experimental example 2.
Figure 19B:
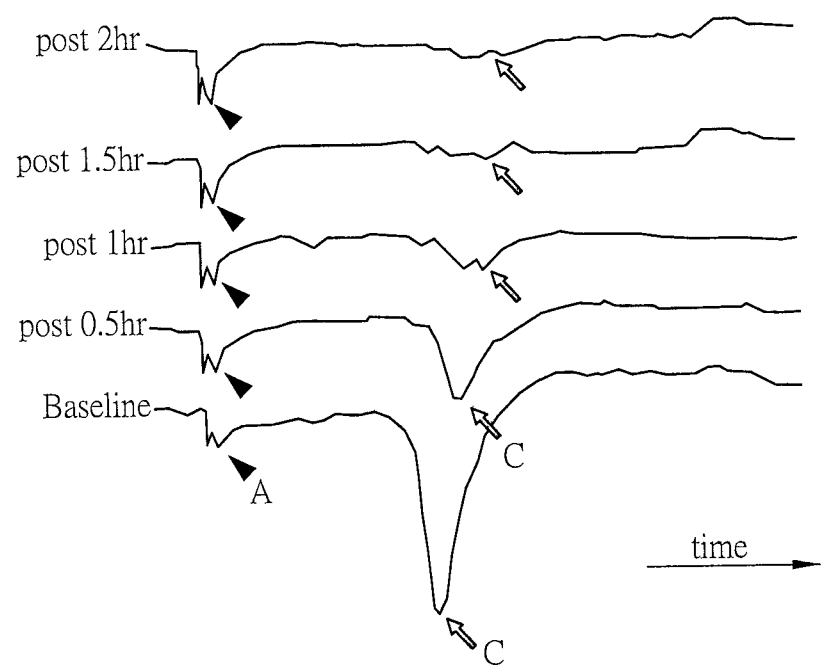

In this experiment, as to the rats receiving the electrical stimulation for 5 minutes, the mean values of the neural responses for every 30 minutes are aligned at the point of 90 ms first, and then the individual time of each group are compared. Referring to FIG. 19A and FIG. 19B, the mean lines of interval of every 30 minutes are put together for comparison. Here, there are no significant differences between the curves of individual time in the control group shown in FIG. 19A. Compared with the control group, it can be seen from FIG. 19B that the C-component is relatively largely reduced after the electrical stimulation in comparison with the baseline in the experimental group.

In detail, the large current stimulation on the peripheral sciatic nerve acts as the source of pain in this experimental example, and the signal can be transmitted to the dorsal root ganglion and the spinal dorsal root nerves through A-fibers and C-fibers by nerve conduction. The neural response to the interventional measure of electrical stimulation can be observed by electrophysiological measurement of nerve conduction. From FIG. 19B, the induced C response is relatively largely reduced with time after receiving the electrical stimulation, and the area of the C-component (intensity) is also reduced with time. It shows that the axon of the C-fiber which is responsible for sense of pain (especially the pain which is chronic and difficult to locate) is changed in transmission. The electrical stimulation blocks or inhibits the signal transmission of neuron in some fibers, so the pain can be relieved, even totally blocked.

Experimental Example 3: Spasticity Reducing Test

Figure 20A:
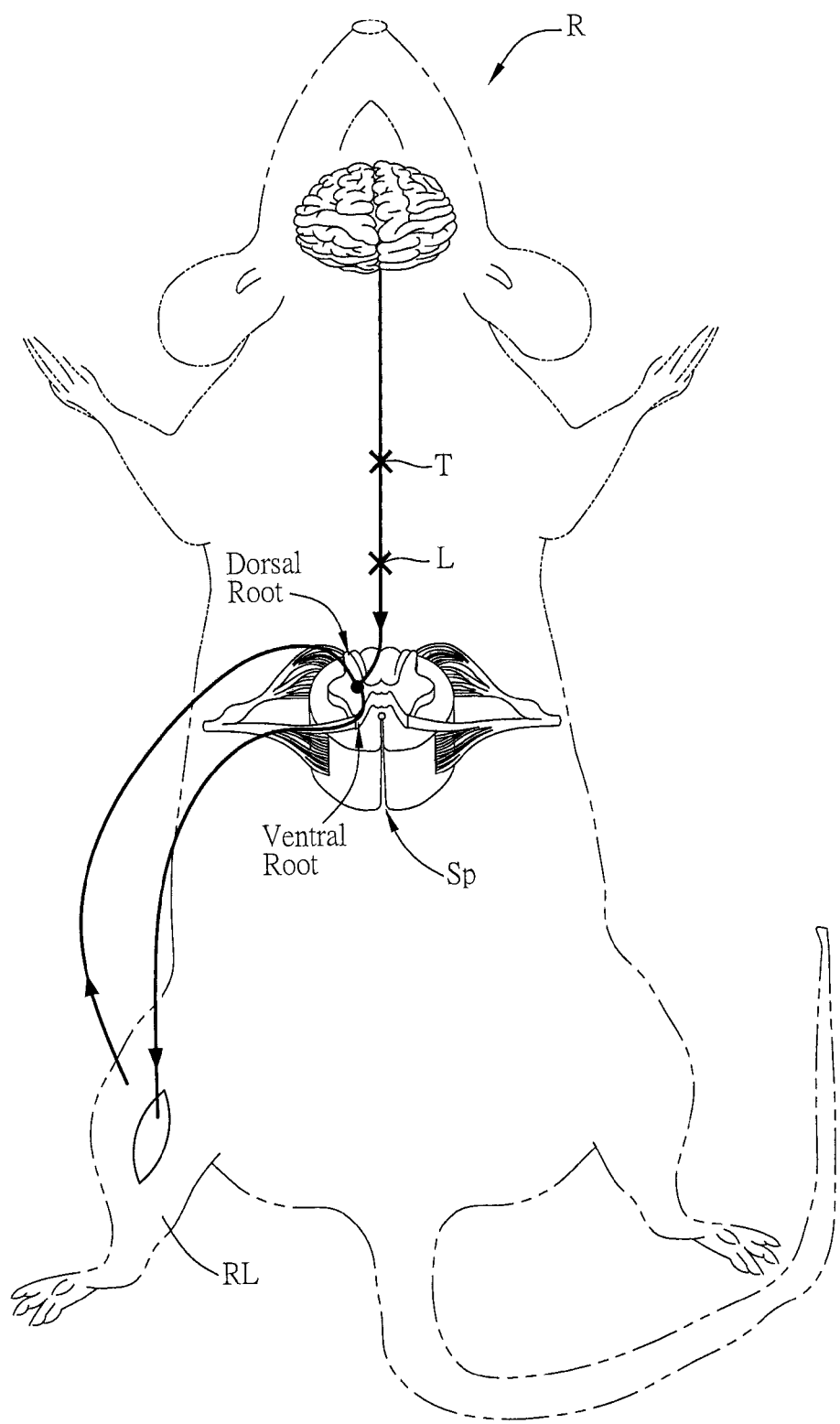
FIG. 20A is a schematic diagram showing the SCI (spinal cord injury) rat model in the spasticity reducing test according to Experimental example 3.
Figure 20B:
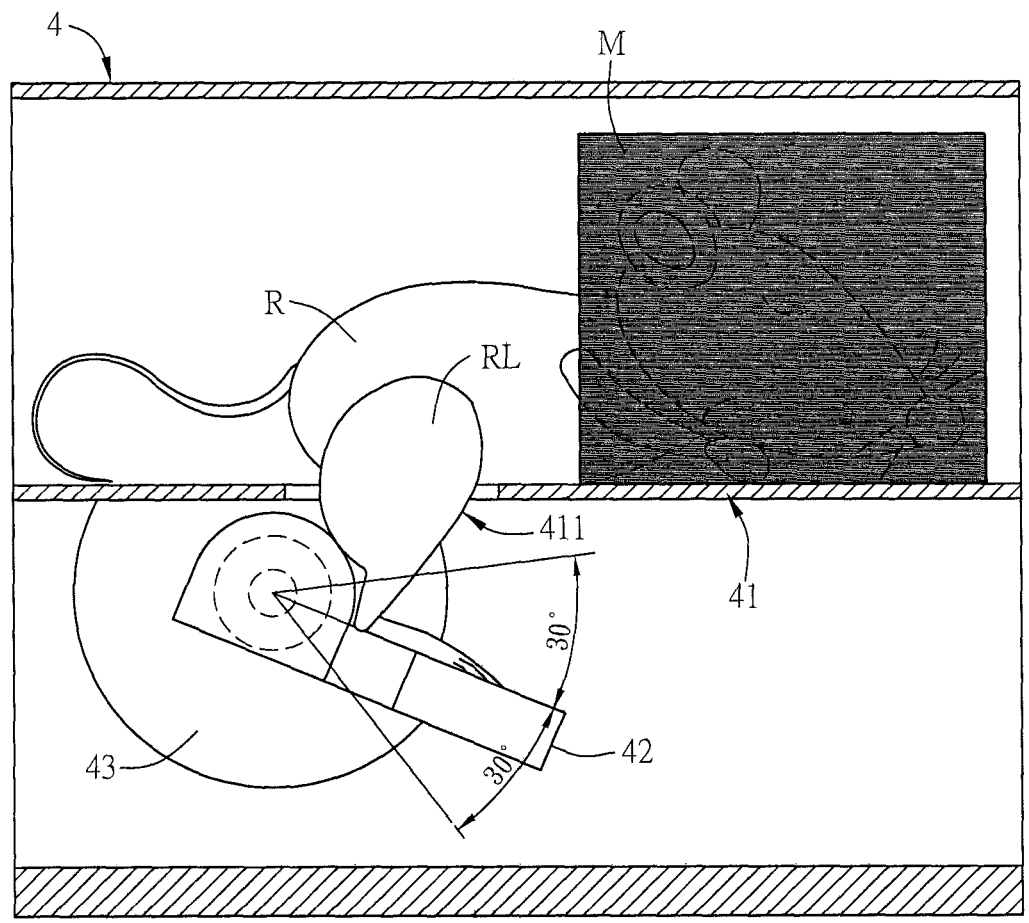
FIG. 20B is a schematic diagram showing the measuring system used in the spasticity reducing test according to Experimental example 3.

The electrical stimulation device provided by the above-mentioned embodiments of the present invention can be used to reduce pain and also can be used to reduce spastic symptoms of an organism. Please referring to FIGS. 20A and 20B. FIG. 20A is a schematic diagram showing the SCI (spinal cord injury) rat model in the spasticity reducing test according to the present Experimental example. FIG. 20B is a schematic diagram showing the measuring system used in the spasticity reducing test according to the present Experimental example. In the present Experimental example, rats R receive the first electrical stimulation signal delivered by the electrical stimulation unit of the electrical stimulation device provided by the above-mentioned embodiments of the present invention, to demonstrate the efficacy of the electrical stimulation device applied for reducing spasticity.

As shown in FIG. 20A, the neurotransmission pathway of the rat R includes the spinal cord Sp, dorsal root, ventral root, and brain of the rat. The injured location of the nerve is labelled as T and the location of the electrical stimulation is labelled as L. After receiving the surgery of spinal cord injury, rat R tends to show spastic symptoms, such as involuntary movement of its leg RL, so as to mimic the organism who suffered from spasticity.

In the present Experimental example, SD rats of about 275-350 grams weight are used (BioLASCO, Taiwan co., Ltd., Taiwan) and they are provided from the central laboratory animal center of Shin Kong Wu Ho-Su Memorial Hospital. The SD rats are divided into the experimental group and the control group (sham group). According to the process provided by Pascale Boulenguez (Pascale Boulenguez et al. (2010, March), Down-regulation of the potassium-chloride cotransporter KCC2 contributes to spasticity after spinal cord injury, NATURE MEDICINE, 16(3), 308), the SD rats of the experimental group and the control group were anesthetized and followed by laminectomy. After laminectomy, the SD rats were transected the right-side segment of the spinal cord at the thoracic level (T5-T6) to remove the sensing neurons and the motion neurons thereof. The electrical stimulation unit was implanted at the L5 dorsal ganglion root of each SD rat. The SD rats of the experimental group received the electrical stimulation for 5 minutes. The frequency of the first electrical stimulation signal is 500 KHz. The duration time Td of the pulses in single pulse period is 25 milliseconds. The preset voltage applied across the first electrode and the second electrode is ±5V, and pulse-repetition frequency (PRF) is 2 Hz. The SD rats of the control group did not receive any electrical stimulation.

The muscle tone of the SD rats of the experimental group and the control group are assessed according to the measuring method and measuring system provided by T. H. Hsieh (T. H. HSIEH et al. (2010), Time course quantification of spastic hypertonia following spinal hemisection in rats, NEUROSCIENCE, 167, 187-188).

As shown in FIG. 20B, the measuring system 4 comprises a platform 41, peddle 42, and a motor 43. An opening 411 is disposed below the platform 41, and the leg RL of the SD rat R can extend to the outside of the platform through the opening 411 and is placed on the peddle 42. The peddle 42 is coupled to a torsionmeter. The head of the SD rat R are covered by mask M to reduce the interference from external environment. The motor 43 made the peddle swinging up and down, so as to make the paws of the leg RL of the SD rat R do the motion of dorsiflexion and plantarflexion repetitively. The amplitude of the swing of the peddle 42 is between ±30 degrees from its rest position. The leg RL of the SD rat R would have spasticity due to continuous swings of the peddle 42 and became hard to make a flexion and an extension motion. Accordingly, it would take a greater torque to make the paw of the SD rat R to do the dorsiflexion and plantarflexion continuously, and the torque value (e.g., the muscle tone of the SD rat R) measured by the torsionmeter was increased.

The muscle tone of SD rats of the experimental group and the control group were measured and recorded at the following time points: the 0 day before SCI surgery (Normal 0), 28 days after SCI surgery (SCI d28), and 3 days (PRF d3), 7 days (PRF d7), and 14 days (PRF d14) after the electrical stimulation. The rotation speed of the motor (e.g., the swing speed of the peddle) is 25 rpm or 75 rpm.

Figure 20C:
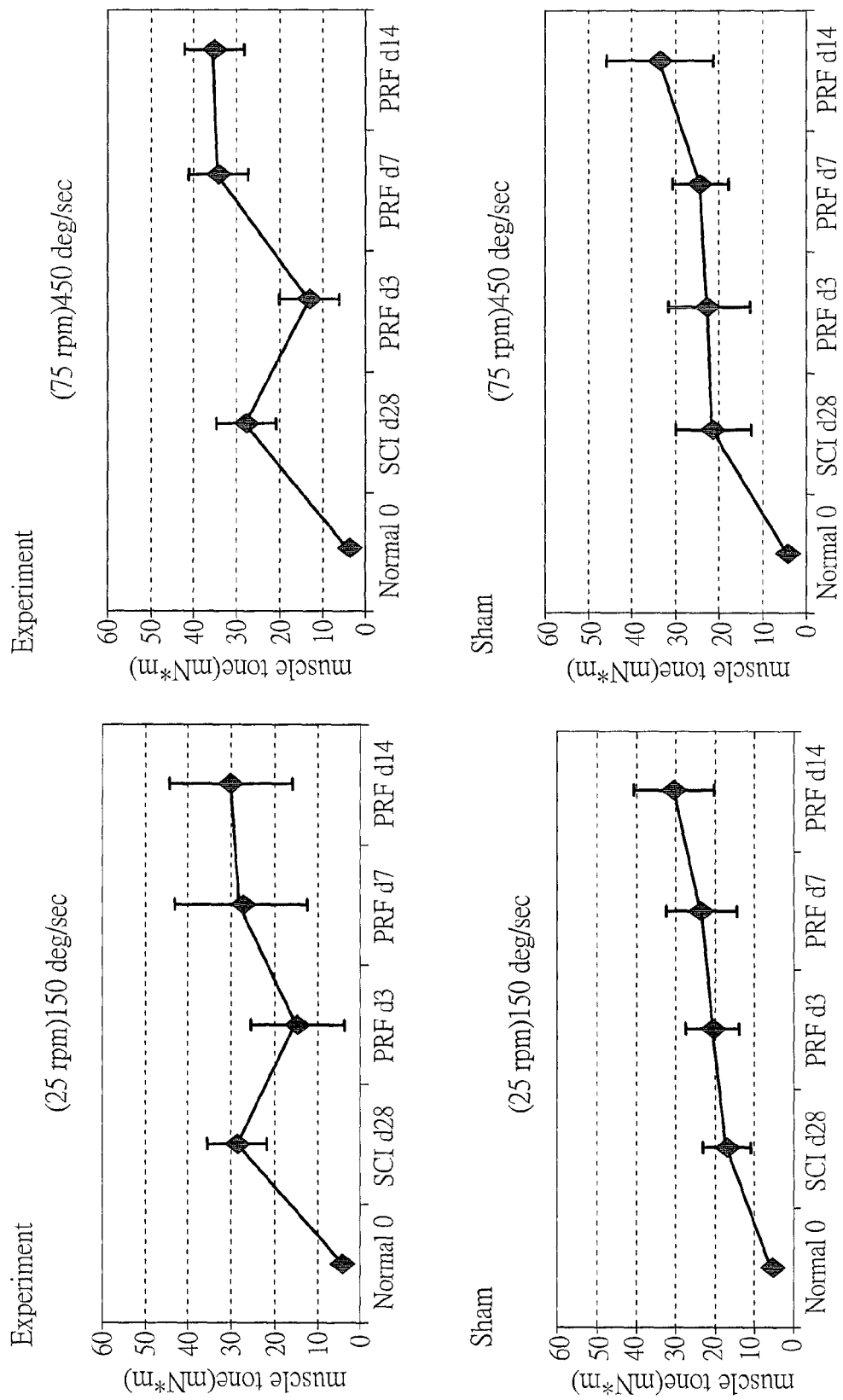
FIG. 20C is the muscle tone assessment results of the normal rats of the control group and the SCI rats of the experimental group according to Experimental example 3.
Figure 20D:
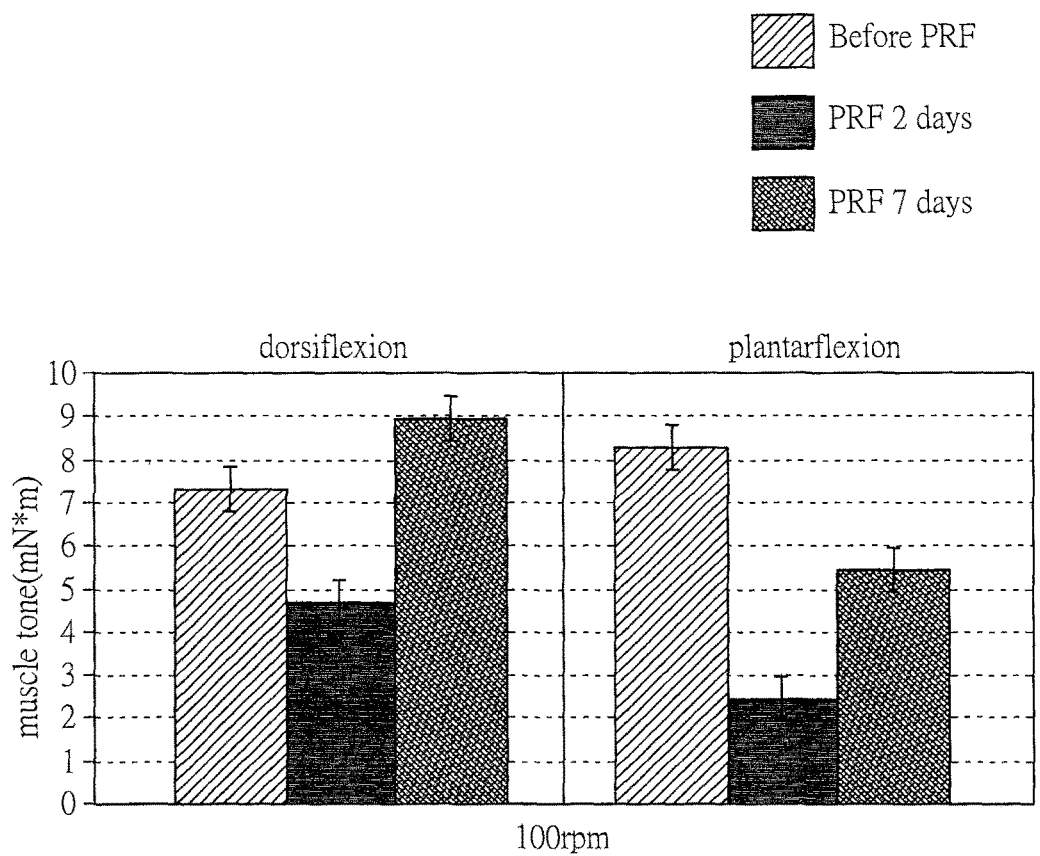
FIG. 20D is the muscle tone assessment results (dorsiflexion and plantarflexion) of the SCI rats according to Experimental example 3.

The muscle tone assessment results were shown in FIGS. 20C and 20D. As shown in FIG. 20C, when the peddle swung at a speed of 25 rpm (150 deg/sec) or 75 rpm (450 deg/sec), the muscle tones of the SD rats in the experimental group and the control group were increased (the experimental group is increased to about 29 mN-m, and the control group is increased to about 17 mN-m) at 28 days after SCI surgery (SCI d28). It means that the SD rats had obvious spastic symptoms after SCI surgery.

At 3 days after electrical stimulation (PRF d3), the muscle tones of the SD rats in the experimental group is lowered when compared with those measured before electrical stimulation (SCI d28). In the meantime, the muscle tones of the SD rats in the control group still increased continuously. Such result demonstrates that the spastic symptoms of the SD rats in the experimental group are actually ameliorated after receiving the electrical stimulation. On the contrary, the spastic symptoms of the SD rats in the control group did not have any improvements at the same time.

As shown in FIG. 20D, in the motion of dorsiflexion and plantarflexion, the muscle tones of the SD rats in the experimental group were dropped at 2 days (PRF d2) after the electrical stimulation (about 4.8 mN-m for dorsiflexion and about 2.5 mN-m for plantarflexion) when compared to those measured before the electrical stimulation (SCI d28). This result also demonstrates that the spastic symptoms of the SD rats in the experimental group are actually ameliorated after receiving the electrical stimulation. Even at 7 days (PRF d7) after the electrical stimulation, the muscle tones of the SD rats in the experimental group were still lower than those measured before the electrical stimulation, which was about 5.3 mN-m. This result demonstrates that the method according to the embodiment of the present invention has a long-term effect to reduce the spastic symptoms of an organism.

Experimental Example 4: Long-Term Effect of PRF Electrical Stimulation on Pain Behaviors in SD Rats SD rats were divided into 3 groups: the normal (didn't received SNL) with sham PRF group (C+Sham), the SNL (received SNL on L5) with sham PRF group (SNL+Sham), and the SNL with PRF group (SNL+PRF). The spinal nerve ligation (SNL) is performed on the L5 spinal nerves of the SD rats of the SNL+Sham group and the SNL+PRF group. Only SD rats in the SNL+PRF group are received PRF stimulations, which are performed as following: the stimulation electrode was inserted into the left L5 for aminal canal, whereas the reference electrode was placed in contact with the surrounding non-neural tissues. The electrodes were connected to a PXI-5402 Function Generator (National Instruments, Austin, Tex.) to generate RF pulses with the following parameter settings based on clinical settings: 2-Hz biphasic trains with 500-kHz RF waves, 25-ms train width, and oscillating amplitudes at an intensity of 2.5 V. The PRF duration was 300 seconds. SD rats of the SNL+Sham group are received an electrode placement without electricity as a sham stimulation. The PRF stimulation or sham PRF stimulation was performed 8 days after the spinal nerve ligation (SNL+PRF, or SNL+Sham, respectively).

The mechanical threshold was evaluated using von Frey filaments (Stoelting, Wood Dale, Ill.) as described in the Experimental example 1. The tests were conducted daily from at least 2 days before SNL for establishing preoperative baselines, and scheduled days after SNL as well as after PRF/sham treatment.

The thermal threshold was measured by paw withdrawal latencies to radiant heat stimulation in the plantar test device (Plantar Test Apparatus, IITC, CA). The cut-off latency was 30 seconds to avoid thermal injury. The withdrawal latency at each time point was an average of three latencies separated by a 5-min interval. The tests were conducted on the same days as the von Frey test and both tests were conducted by the same operator who was blinded to the group allocation.

Figure 21A:
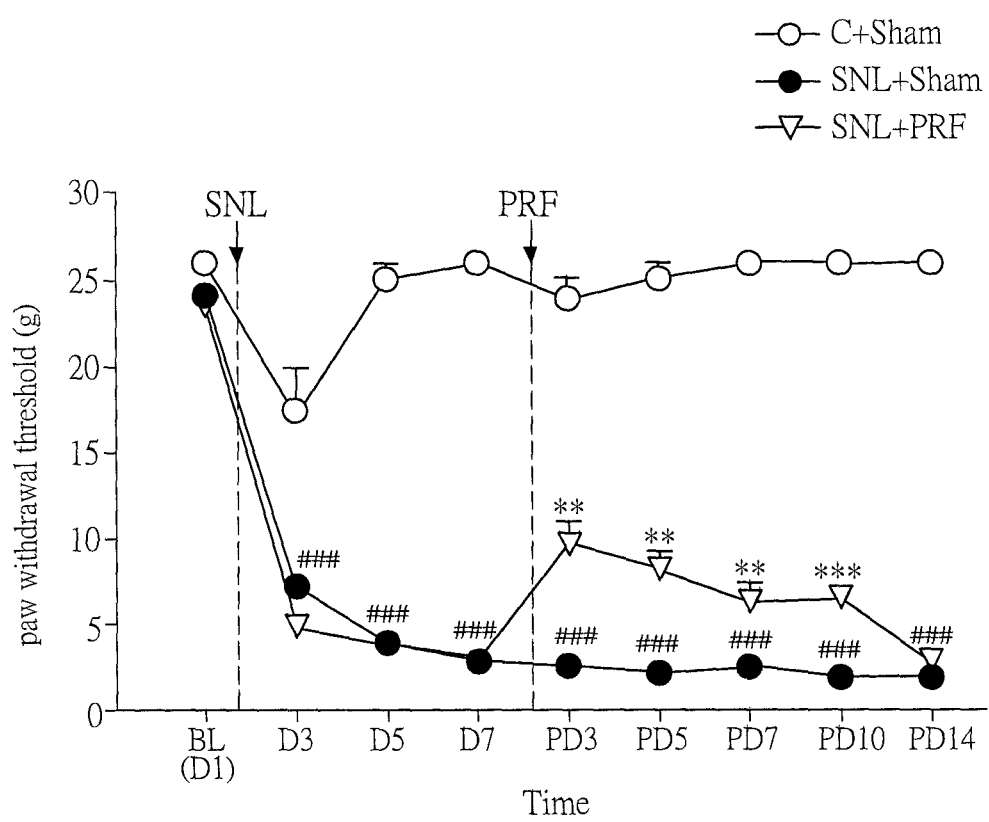
FIGS. 21A and 21B are the results illustrating long-term effect of PRF electrical stimulation on pain behaviors in SD rats according to Experimental example 4.
Figure 21B:
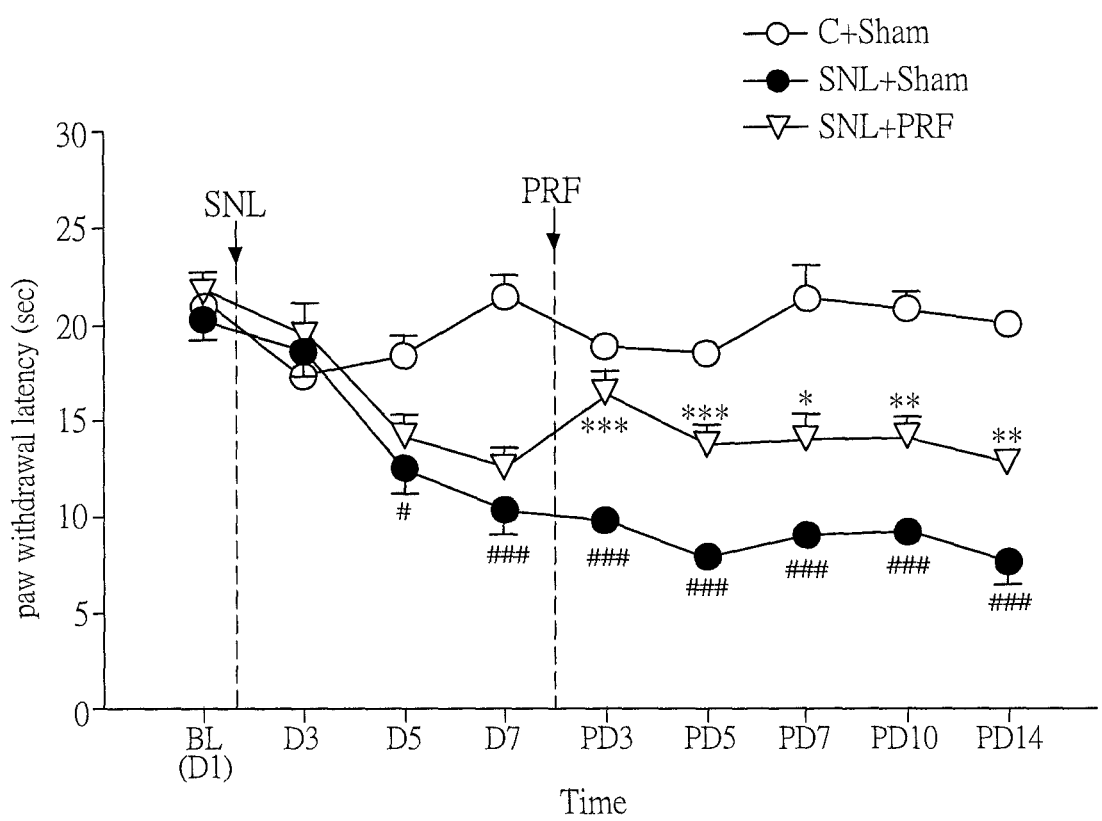

The effect of the PRF stimulation on SNL-induced mechanical allodynia and heat hyperalgesia are shown in FIGS. 21A and 21B, respectively. The arrows indicate spinal nerve ligation and PRF stimulation. "BL" means pre-SNL baseline, "Dn" means post-SNL day, and "PDn" means (PRF/sham) posttreatment day. * $P<0.05$,  $P<0.01$, * $P<0.001$ for SNL+PRF versus SNL+sham; # $P<0.05$, ### $P<0.001$ for SNL+sham versus C+sham by one-way ANOVA with the post hoc test.

From the results shown in both FIGS. 21A and 21B, SNL resulted in drastically mechanical and thermal hypersensitivities (SNL+Sham group in FIGS. 21A and 21B; $P=0.000$ for most post-SNL data vs baseline data; and $P<0.001$ for SNL+Sham vs C+Sham, which are not shown). When compared with the results of SNL+Sham group, the PRF stimulations significantly suppressed mechanical allodynia (i.e., tactile allodynia) for 10 days ($P<0.005$ at PD10; FIG. 21A) of SNL+PRF group, and also reduced thermal hyperalgesia for 2 weeks ($P<0.01$ at PD14; FIG. 21B) of SNL+PRF group. It demonstrates that the PRF stimulations of the present embodiment exert effects on the late-stage pain. Collectively, FIGS. 21A and 21B illustrates that the PRF electrical stimulations produced prolonged analgesic effect on SNL-induced pain at least for 1, 2, 3, 4, 5, 6, 7, 8, 9, 10, 11, 12, 13, and 14 days.

Moreover, according to at least the results of the Experimental example 2 (FIGS. 19A and 19B), the C-response continuously reduced in the first two hours after the PRF electrical stimulation and became stable afterwards. Such result represents that the PRF electrical stimulation can exert effect of pain relief at least for two hours. In combination of the results of the Experimental example 1, 2 and 4 (FIGS. 18A, 18B, 19A, 19B, 21A and 21B), the effect of pain relief exerted by the PRF electrical stimulations of the present embodiments can last for 2, 4, 6, 8, 10, 12, 14, 16, 18, 20, or 22 hours, or 1, 2, 3, 4, 5, 6, 7, 8, 9, 10, 11, 12, 13 or 14 days after receiving PRF electrical stimulations. At 14 days after receiving PRF electrical stimulations, the paw withdrawal thresholds of the experimental group returned to about the same level as the control or sham group. Such results also represent that the effects exerted by the PRF electrical stimulations of the present embodiments are recoverable and do not lead to permanent damage of the targeted nerves.

In other words, the electrical stimulation device and method can be applied to reduce the spastic symptoms and have a long-term efficacy. In addition to effectively ameliorate the spastic symptoms of an organism, it would not have to take too much time to use such electrical stimulation device and method. Other technical features of the method for reducing spasticity utilizing the electrical stimulation device of the embodiments of the present invention are substantially the same as those describe above, and they are not repeated here.

In summary, in the method for reducing spasticity and the non-transitory computer-readable medium according to the disclosure, a first electrical stimulation signal is delivered by the electrical stimulation unit of the electrical stimulation device so as to generate an electric field between the first electrode and the second electrode. The electric field covers a target zone of an organism who suffers from spasticity. Such method and non-transitory computer-readable medium can effectively ameliorate spastic symptoms with long term effects, without the side effects caused by drugs, and also reduce the possibility of infection caused by operation.

Although the invention has been described with reference to specific embodiments, this description is not meant to be construed in a limiting sense. Various modifications of the disclosed embodiments, as well as alternative embodiments, will be apparent to persons skilled in the art. It is, therefore, contemplated that the appended claims will cover all modifications that fall within the true scope of the invention.

What is claimed is:

1. A method for reducing spasticity applied to electrically stimulate a target zone of an organism by an implanted electrical stimulation device, wherein the implanted electrical stimulation device includes at least an electrical stimulation unit, the method comprising:

placing the electrical stimulation unit including at least a first electrode and a second electrode near the target zone wherein the target zone is a dorsal root ganglion, a spinal cord, a dorsal root, a ventral root or a nerve on a neurotransmission pathway causing spastic symptoms; and delivering a first electrical stimulation signal by the electrical stimulation unit of the implanted electrical stimulation device to electrically stimulate the target zone without nerve blocking agent, wherein an electric field covering the target zone is generated between the first electrode and the second electrode of the implanted electrical stimulation device according to the first electrical stimulation signal, and a strength of the electric field is larger than 100 V/m and smaller than 1000 V/m so as to reduce spasticity of the organism.

2. The method according to claim 1, wherein the first electrical stimulation signal is a pulse signal and its pulse repetition frequency ranges from 0 to 1 KHz.

3. The method according to claim 1, wherein the frequency of the first electrical stimulation signal ranges from 200 KHz to 1000 KHz.

4. The method according to claim 3, wherein the frequency of the first electrical stimulation signal ranges from 200 KHz to 450 KHz or ranges from 550 KHz to 1000 KHz.

5. The method according to claim 1, wherein the frequency of the first electrical stimulation signal comprises a plurality of pulse signals, and the plurality of pulse signals have a duration time ranging from 1 to 250 ms.

6. The method according to claim 1, wherein the voltage of the first electrical stimulation signal ranges from −10V to −1V or ranges from 1V to 10V.

7. The method according to claim 1, wherein the current of the first electrical stimulation signal ranges from 2 mA to 50 mA.

8. The method according to claim 1, wherein the first and second electrodes are separated by a first distance which ranges from 3 mm to 7 mm, and the first and second electrodes are at least at a second distance away from the target zone, and the second distance is no more than 10 mm.

9. The method according to claim 1, wherein the first electrical stimulation signal is adapted to block the neurotransmission in the target zone.

10. The method according to claim 1, wherein the electrical stimulation unit further delivers a low electrical stimulation signal which is not higher than 1 KHz.

11. The method according to claim 1, wherein the organism receives the electrical stimulation signal for a second time at least 24 hours after receiving the electrical signal for a first time.

12. The method according to claim 1, wherein the first electrical stimulation signal is adapted to block the neurotransmission in the target zone by blocking or inhibiting c-fibers.

13. A non-transitory computer-readable medium storing one or more instructions configured to be executed by an implanted electrical stimulation device to electrically stimulate a target zone of an organism who suffers from spasticity so as to reduce spasticity of the organism, wherein the implanted electrical stimulation device includes at least an electrical stimulation unit, and the electrical stimulation unit includes at least a first electrode and a second electrode, and when the instructions are executed by the implanted electrical stimulation device, the implanted electrical stimulation device executes a plurality steps comprising:

delivering a first electrical stimulation signal by the electrical stimulation unit of the implanted electrical stimulation device to electrically stimulate the target zone without nerve blocking agent wherein the target zone is a dorsal root ganglion, a spinal cord, a dorsal root, a ventral root or a nerve on a neurotransmission pathway causing spastic symptoms, wherein an electric field covering the target zone is generated between the first electrode and the second electrode of the implanted electrical stimulation device according to the first electrical stimulation signal, and a strength of the electric field is larger than 100 V/m and smaller than 1000 V/m so as to reduce spasticity of the organism.

14. The non-transitory computer-readable medium according to claim 13, wherein the first electrical stimulation signal is a pulse signal and its pulse repetition frequency ranges from 0 to 1 KHz.

15. The non-transitory computer-readable medium according to claim 13, wherein the frequency of the first electrical stimulation signal ranges from 200 KHz to 1000 KHz.

16. The non-transitory computer-readable medium according to claim 13, wherein the first electrical stimulation signal is adapted to block the neurotransmission in the target zone by blocking or inhibiting c-fibers.

17. A method for reducing spasticity applied to electrically stimulate a target zone of an organism by an implanted electrical stimulation device, wherein the implanted electrical stimulation device includes at least an electrical stimulation unit, the method comprising:

placing the electrical stimulation unit including at least a first electrode and a second electrode near the target zone wherein the target zone is a dorsal root ganglion, a spinal cord, a dorsal root, a ventral root or a nerve on a neurotransmission pathway causing spastic symptoms; and delivering a first electrical stimulation signal by the electrical stimulation unit of the implanted electrical stimulation device to electrically stimulate the target zone without destroying the neural cells, wherein an electric field covering the target zone is generated between the first electrode and the second electrode of the implanted electrical stimulation device according to the first electrical stimulation signal, and the frequency of the first electrical stimulation signal ranges from 200 KHz to 1000 KHz so as to reduce spasticity of the organism.

18. A non-transitory computer-readable medium storing one or more instructions configured to be executed by an implanted electrical stimulation device to electrically stimulate a target zone of an organism who suffers from spasticity so as to reduce spasticity of the organism, wherein the implanted electrical stimulation device includes at least an electrical stimulation unit, and the electrical stimulation unit includes at least a first electrode and a second electrode, and when the instructions are executed by the implanted electrical stimulation device, the implanted electrical stimulation device executes a plurality steps comprising:

delivering a first electrical stimulation signal by the electrical stimulation unit of the implanted electrical stimulation device to electrically stimulate the target zone without destroying the neural cells wherein the target zone is a dorsal root ganglion, a spinal cord, a dorsal root, a ventral root or a nerve on a neurotransmission pathway causing spastic symptoms, wherein an electric field covering the target zone is generated between the first electrode and the second electrode of the implanted electrical stimulation device according to the first electrical stimulation signal, and the frequency of the first electrical stimulation signal ranges from 200 KHz to 1000 KHz so as to reduce spasticity of the organism.

* * * * *